(12) United States Patent
Yang et al.

(10) Patent No.: US 10,006,008 B2
(45) Date of Patent: *Jun. 26, 2018

(54) RECOMBINANT MICROORGANISM HAVING ENHANCED ABILITY TO PRODUCE 2,3-BUTANEDIOL AND METHOD FOR PRODUCING 2,3-BUTANEDIOL USING SAME

(71) Applicant: GS CALTEX CORPORATION, Seoul (KR)

(72) Inventors: Taek-Ho Yang, Daejeon (KR); Hyo-Hak Song, Daejeon (KR); Jong-Myoung Park, Sejong (KR); Chelladural Rathnasi, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/025,521

(22) PCT Filed: Sep. 26, 2014

(86) PCT No.: PCT/KR2014/009067
§ 371 (c)(1),
(2) Date: Mar. 28, 2016

(87) PCT Pub. No.: WO2015/046978
PCT Pub. Date: Apr. 2, 2015

(65) Prior Publication Data
US 2016/0244730 A1    Aug. 25, 2016

(30) Foreign Application Priority Data

Sep. 27, 2013    (KR) .......................... 10-2013-0115682

(51) Int. Cl.
*C12N 9/04*    (2006.01)
*C12P 7/18*    (2006.01)

(52) U.S. Cl.
CPC .............. *C12N 9/0006* (2013.01); *C12P 7/18* (2013.01)

(58) Field of Classification Search
None
See application file for complete search history.

(56) References Cited

U.S. PATENT DOCUMENTS

| 6,413,765 B1 | 7/2002 | Walfridsson et al. |
| 2010/0112655 A1 | 5/2010 | Paul |

FOREIGN PATENT DOCUMENTS

| KR | 1020120128776 A | 11/2012 |
| WO | 2010/037114 A1 | 4/2010 |

OTHER PUBLICATIONS

Bottcher et al., Appl. Microbiol. Biotechnol. 73: 1282-1289, 2007.*
International Search Report dated Dec. 12, 2014 corresponding to International Application No. PCT/KR2014/009067.
Xiao-Jun Ji et al., "Microbial 2,3-Butanediol Production: A State-of-the-Art Review", Biotechnology Advances., 2011, 29: 351-364.
E. Celińska et al., "Biotechnological Production of 2,3-Butanediol-Current State and Prospects", Biotechnology Advances, 2009, 27: 715-725.
Xiao-Jun Ji et al., "Enhanced 2,3-Butanediol Production by Klebsiella Oxytoca Using a Two-Stage Agitation Speed Control Strategy", Bioresource Technology, 2009, 100:3410-3414.
Yutaka Nakashimada et al., "Enhanced 2,3-Butanediol Production by Addiction of Acetic Acid in Paenibacillus polymyxa", Journal of Bioscience and Bioengineering, 2000, vol. 90, No. 6, pp. 661-664.
Y. Nakashimada et al., "Optimization of Dilution Rate, pH and Oxygen Supply on Optical Purity of 2, 3-Butanediol Produced by Paenibacillus polymyxa in Chemostat Culture", Biotechnology Letters, Dec. 2, 1998, vol. 20, No. 12, pp. 1133-1138.
Xiao-Jun Ji et al., "Enhanced 2,3-Butanediol Production by Altering the Mixed Acid Fermentation Pathway in Klebsiella Oxytoca", Biotechnology Letters, 2008, 30:731-734.
Cuiqing Ma et al., "Enhanced 2,3-Butanediol Production by Klebsiella Pneumoniae SDM", Appl. Microbiol. Biotechnol., 2009, 82: 49-57.
Xao-Jun Ji et al., "Engineering Klebsiella Oxytoca for Efficient 2,3-Butanediol Production Through Insertional Inactivation of Acetaldehyde Dehydrogenase Gene", Appl. Microbiol. Biotechnol., 2010, 85: 1751-1758.
GenBank Accession No. CP003683, Klebsiella oxytoca E718, complete genome,Sep. 12, 2012, pp. 1-610.
GenBank Accession No. WP_004124794, Multispecies: diacetyl reductase [Klebsiella], Aug. 29, 2013. pp. 1/1.

* cited by examiner

*Primary Examiner* — Nancy A Treptow

(74) *Attorney, Agent, or Firm* — Hauptman Ham, LLP

(57) ABSTRACT

The present invention relates to a gene which codes an enzyme having conversion activity between acetoin and 2,3-butanediol and has a nucleotide sequence of SEQ ID NO: 12. Further, the present invention relates to a protein coded by the gene. Further, the present invention relates to a recombinant microorganism having suppressed activity of the protein.

5 Claims, 13 Drawing Sheets

RECOMBINANT MICROORGANISM HAVING ENHANCED ABILITY TO PRODUCE 2,3-BUTANEDIOL AND METHOD FOR PRODUCING 2,3-BUTANEDIOL USING SAME

CROSS REFERENCE TO RELATED APPLICATION

This application claims the priority of Korean Patent Application No. 10-2013-0115682, filed on Sep. 27, 2013 in the KIPO (Korean Intellectual Property Office). Further, this application is the National Phase application of International Application No. PCT/KR2014/009067 filed Sep. 26, 2014, which designates the United States and was published in Korea.

TECHNICAL FIELD

The present invention relates to a recombinant microorganism having an enhanced ability to produce 2,3-butanediol and a method for producing 2,3-butanediol using the same.

BACKGROUND ART 2,3-butanediol is an alcohol (represented by $CH_3CHOHCHOHCH_3$) having four carbons and two hydroxyl (—OH) groups and can be chemically and catalytically converted into 1,3-butadiene, which is a raw material for preparation of synthetic rubbers, and methyl ethyl ketone (MEK), which is a fuel additive and a solvent (Ji et al., Biotechnol. Adv., 29: 351, 2011). 2,3-butanediol is a very important industrial intermediate since 2,3-butanediol can be used as an octane booster through mixing with gasoline (Celinska et al., Biotechnol. Adv., 27: 715, 2009).

2,3-butanediol can be produced by chemical synthesis and microbial fermentation. However, due to high production costs, 2,3-butanediol has not been produced on a commercially viable scale. In recent years, with the rapid development of techniques for producing 2,3-butanediol through microbial fermentation, price surge for fossil fuel derivatives, and tightened international regulations on environmental contamination, there has been a growing focus on the importance of finding bio-based methods for producing 2,3-butanediol through microbial fermentation.

Research into bio-based methods for producing 2,3-butanediol through microbial fermentation has been performed in divided categories such as optimization of fermentation processes (temperature, pH, dissolved oxygen, and the like) and searching for microorganisms (identification of microorganisms, characterization of physiological properties of identified microorganisms, performing mutation and genetic engineering, and the like). In view of optimization of fermentation processes, various conditions for ensuring effective production of 2,3-butanediol, such as temperature, pH, dissolved oxygen concentration, and the like have been identified (Ji et al., Bioresour. Technol., 100: 3410, 2009; Nakashimada et al., J. Biosci. Bioeng., 90: 661, 2000; Nakashimada et al., Biotechnol. Lett., 20: 1133, 1998). However, production of 2,3-butanediol through microbial fermentation under these conditions still has problems of low productivity and yield, which makes direct application thereof to commercial processes difficult. Furthermore, such fermentation has a disadvantage in that various byproducts such as organic acids including lactic acid, alcohols including ethanol, and the like are produced together with 2,3-butanediol during fermentation.

Production of byproducts not only lowers yield of 2,3-butanediol as compared with raw biomaterials, but also requires great cost for separation and purification of 2,3-butanediol upon harvesting 2,3-butanediol from the culture solution. Accordingly, the development of microorganisms related to production of 2,3-butanediol has been performed in a direction of decreasing byproducts. Ji et al., have succeeded in partially suppressing production of organic acids as byproducts by exposing a wild type *Klebsiella oxytoca* to ultraviolet radiation (UV) as a physical/chemical mutation method (Ji et al., Biotechnol. Lett., 30: 731, 2008). Further, it was possible to enhance production of 2,3-butanediol by applying ion beams to *Klebsiella pneumonia*, thereby increasing biomass consumption rate (Ma et al., Appl. Microbiol. Biotechnol., 82: 49, 2009). In research relating to byproduct reduction through selective genetic engineering, mutant microorganisms made by deleting a gene (ldhA) responsible for production of lactic acid as one of major byproducts exhibited the best performance under general conditions. In addition, there have been examples that genes (adhE, aldA) responsible for production of ethanol are deleted in order to decrease production of ethanol as a byproduct (Ji et al., Appl. Microbiol. Biotechnol., 85: 1751, 2010). In some examples, the activity of pyruvate formate lyase responsible for generating formic acid in lactic acid bacteria (LAB) is decreased (WO2010/037114 A1).

The present inventors have identified a gene having conversion activity on 2,3-butanediol, and have also identified that recombinant microorganisms in which the activity of the gene is suppressed show an enhanced ability to produce 2,3-butanediol and consumption of the produced 2,3-butanediol is prohibited. Based on this finding, the present invention has been completed.

DISCLOSURE

Technical Problem

It is an aspect of the present invention to provide a recombinant microorganism having an enhanced ability to produce 2,3-butanediol and a method for producing 2,3-butanediol using the same.

Technical Solution

Embodiments of the present invention provide a gene that encodes an enzyme having conversion activity between acetoin and 2,3-butanediol and has a nucleotide sequence of SEQ ID NO: 12.

Embodiments of the present invention provide a recombinant vector including the gene.

Embodiments of the present invention provide a protein encoded by the gene. Furthermore, embodiments of the present invention provide a recombinant microorganism having suppressed activity of the protein.

Embodiments of the present invention provide a recombinant microorganism having an enhanced ability to produce 2,3-butanediol wherein activity of the protein is suppressed in a microorganism having 2,3-butanediol and lactate biosynthetic pathways.

Embodiments of the present invention provide a recombinant microorganism having an enhanced ability to produce 2,3-butanediol, wherein the recombinant microorganism has conversion activity between acetoin and 2,3-butanediol, and an enzyme having a higher activity for converting 2,3- butanediol to acetoin than the activity for converting acetoin to 2,3-butanediol is suppressed in a microorganism having 2,3-butanediol and lactate biosynthetic pathways.

Embodiments of the present invention provide a method for producing 2,3-butanediol including: culturing the recombinant microorganism as set forth above; and harvesting 2,3-butanediol from the culture solution.

Advantageous Effects

A recombinant microorganism according to embodiments of the present invention has an enhanced ability to produce 2,3-butanediol and can decrease a consumption rate of the produced 2,6-butanoldiol. Further, the recombinant microorganism provides a low amount of accumulated acetoin upon culturing.

BEST MODE

Figure 1A:
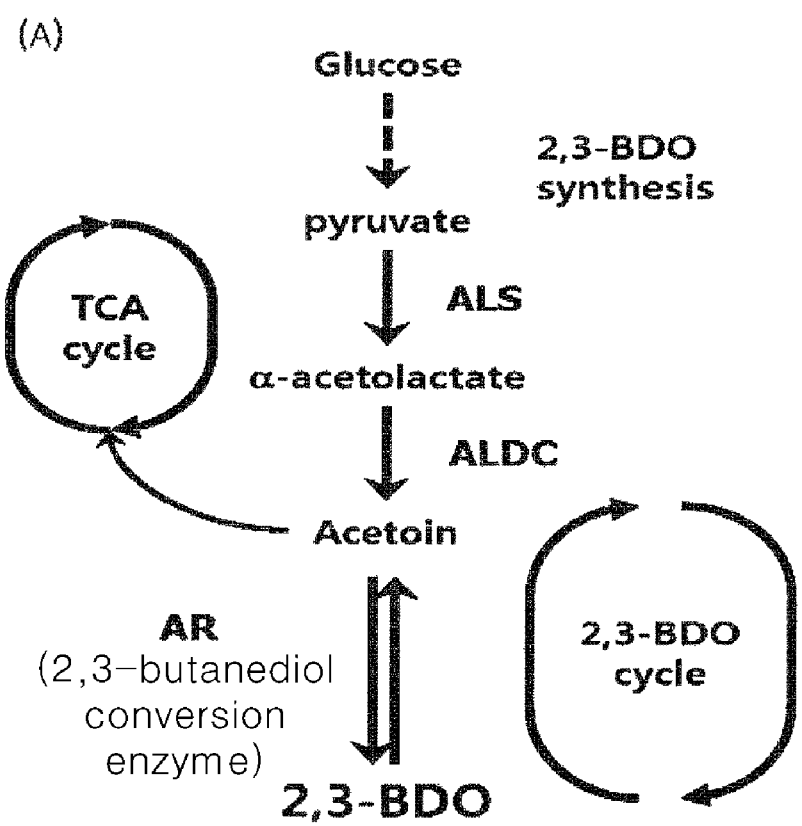
FIG. 1a shows a biosynthetic pathway of 2,3-butanediol in 2,3-butanediol producing strains.

The present invention relates to a gene which encodes an enzyme having conversion activity between acetoin and 2,3-butanediol and has a nucleotide sequence of SEQ ID NO: 12.

The present invention relates to a recombinant vector including the gene.

Further, the present invention relates to a protein encoded by the gene. Furthermore, the present invention relates to a recombinant microorganism having suppressed activity of the protein.

The present invention relates to a recombinant microorganism having an enhanced ability to produce 2,3-butanediol, wherein activity of the protein is suppressed in a microorganism having 2,3-butanediol and lactate biosynthetic pathways.

The present invention relates to a recombinant microorganism having an enhanced ability to produce 2,3-butanediol, wherein the recombinant microorganism has conversion activity between acetoin and 2,3-butanediol, and an enzyme having a higher activity for converting 2,3-butanediol into acetoin than the activity for converting acetoin into 2,3-butanediol is suppressed in a microorganism having 2,3-butanediol and lactate biosynthetic pathways.

The present invention relates to a method for producing 2,3-butanediol including: culturing a recombinant microorganism according to the present invention; and harvesting 2,3-butanediol from the culture solution.

[Mode for Invention]

Hereinafter, embodiments of the present invention will be described in detail.

Conversion Activity Between Acetoin and 2,3-butanediol

The recombinant microorganism according to the present invention has an ability to produce 2,3-butanediol. In the recombinant microorganism according to the present invention, acetoin is converted into 2,3-butanediol, and vice versa. Such metabolic pathways to acetoin and 2,3-butanediol are referred to as conversion activity between acetoin and 2,3-butanediol, particularly mutual transformation activity.

The biosynthetic pathway of 2,3-butanediol is depicted in FIG. 1(A). Most 2,3-butanediol producing strains can utilize 2,3-butanediol as a sole carbon source. At this time, 2,3-butanediol can be consumed using acetoin as an intermediate, as shown in following two pathways. In pathway 2, two molecules of 2,3-butanediol are converted into one molecule of 2,3-butanediol and two molecules of acetic acid through "2,3-butanediol cycle".

<Pathway 1>

Figure 1B:
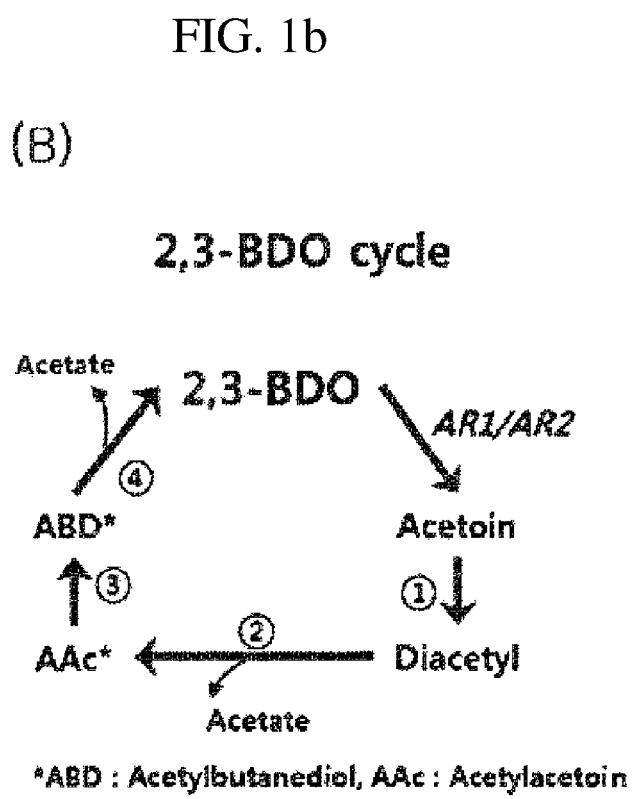
FIG. 1b shows a consumption pathwys of 2,3-butanediol in 2,3-butanediol producing strains.

2,3-butanediol→acetoin→acetaldehyde, acetyl coenzyme A (acetyl-CoA)→TCA pathway (FIG. 1(B)).

<Pathway 2>

Figure 1C:
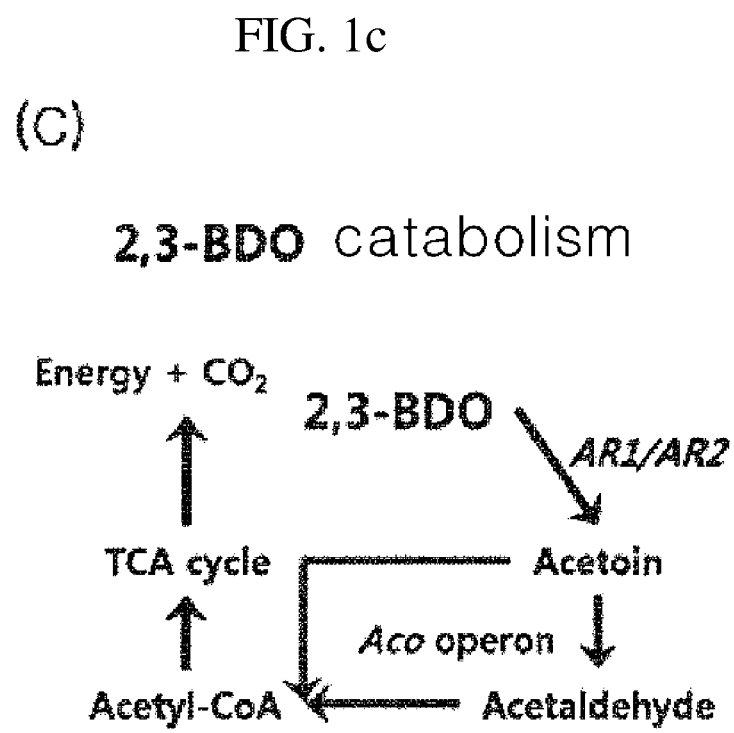
FIG. 1c shows a consumption pathwys of 2,3-butanediol in 2,3-butanediol producing strains.

2,3-butanediol→acetoin→diacetyl→acetic acid, acetylacetone (AAc)→acetic acid and acetylbutanediol (ABD) (FIG. 1(C)).

Gene Having a Nucleotide Sequence of SEQ ID NO: 12

The present invention relates to a gene which encodes an enzyme having conversion activity between acetoin and 2,3-butanediol and has a nucleotide sequence of SEQ ID NO: 12. Further, the present invention relates to a recombinant vector including the gene. The vector may be any vector generally used in the art, such as plasmids and the like, and is not particularly limited.

Further, the present invention relates to a protein encoded by the gene. The protein has an amino acid sequence set forth in SEQ ID NO: 11 or an amino acid sequence having an identity of 90% or more with the amino acid sequence set forth in SEQ ID NO: 11.

Recombinant Microorganism

The recombinant microorganism according to the present invention is a recombinant microorganism having an enhanced ability to produce 2,3-butanediol, wherein the recombinant microorganism has conversion activity between acetoin and 2,3-butanediol, and an enzyme having a higher activity for converting 2,3-butanediol into acetoin than the activity for converting acetoin into 2,3-butanediol is suppressed in a microorganism having 2,3-butanediol and lactate biosynthetic pathways.

Further, the recombinant microorganism according to the present invention is a recombinant microorganism having suppressed activity of the protein which encoded by the gene of SEQ ID NO: 12 in a microorganism having 2,3-butanediol and lactate biosynthetic pathways. The protein encoded by the gene of SEQ ID NO: 12 may be a protein having an amino acid sequence set forth in SEQ ID NO: 11, a protein having an amino acid sequence with 90% or more identity with the amino acid sequence set forth in SEQ ID NO: 11, AR2 protein, or a protein having enzyme activity with 90% or more identity with AR2, and the like.

Activity of the protein may be suppressed by inhibition of expression of the protein, enzyme activity inhibition, and the like. For example, those skilled in the art could easily suppress activity of the protein by selecting suitable methods, such as deleting a gene that encodes the protein, for instance, dar gene, a gene of SEQ ID NO: 12, or a gene having a nucleotide sequence with 90% or more identity with the nucleotide sequence set forth in SEQ ID NO: 12; causing mutations in the gene (mutations such as inhibition of normal gene expression through modifying, substituting or deleting a partial nucleotide sequence or introducing a partial nucleotide sequence); regulating gene expression during transcription or translation, and the like.

The recombinant microorganism according to the present invention may further suppress the pathway of converting pyruvate to lactate. Lactate dehydrogenase regulates the conversion of pyruvate to lactate. The pathway of converting pyruvate to lactate may be suppressed by suppressing lactate dehydrogenase. The suppression of lactate dehydrogenase may be performed by the inhibition of gene expression of lactate dehydrogenase, the inhibition of enzyme activity of lactate dehydrogenase, and the like. For example, those skilled in the art can suppress lactate dehydrogenase by selecting suitable methods, such as deleting a gene that encodes lactate dehydrogenase, for instance, ldhA, causing mutations in the gene (mutations such as inhibition of normal gene expression through modifying, substituting or deleting a partial nucleotide sequence or introducing a partial nucleotide sequence), regulating gene expression during transcription or translation, and the like.

2,3-butanediol conversion enzyme is responsible for production and consumption of 2,3-butanediol. In the recombinant microorganism according to the present invention, the dar gene having high consumption activity is suppressed, and thus consumption of the produced 2,3-butanediol is decreased while maintaining 2,3-butanediol production. Accordingly, the productivity of 2,3-butanediol, namely, the ability to produce 2,3-butanediol is enhanced. In addition, the accumulation of acetoin, which is one of typical byproducts upon production of 2,3-butanediol is also decreased, which leads to cost reduction in separation/purification processes.

The recombinant microorganism is a microorganism having the ability to produce 2,3-butanediol. The recombinant microorganism may be selected from the group consisting of genus *Klebsiella*, genus *Bacillus*, and genus *Enterobacter*. Preferably, the recombinant microorganism is a microorganism belonging to genus *Klebsiella*.

Method for Producing 2,3-butanediol

The present invention relates to a method for producing 2,3-butanediol including: culturing a recombinant microorganism according to the present invention; and harvesting 2,3-butanediol from the culture solution.

Cultivation is performed under aerobic conditions, preferably under microaerobic conditions. For example, the cultivation may be performed by supplying oxygen, namely air, during cultivation. Concretively, the cultivation is performed by stirring, without being limited thereto.

The advantages and features of the present invention and methods for accomplishing the same will become apparent from the following examples. It should be understood that the present invention is not limited to the following examples and may be embodied in different ways, and the following examples are given to provide complete disclosure of the present invention and to provide a thorough understanding of the present invention to those skilled in the art. The present invention should be defined only by the accompanying claims and equivalents thereof.

<Materials and Methods>

Strain of *Klebsiella oxytoca* KCTC 12133BP ΔldhA (KO ΔldhA)

A strain of lactate dehydrogenase gene (ldhA) deleted *Klebsiella oxytoca* KCTC 12133BP ΔldhA (KO ΔldhA) was constructed as follows. Firstly, in order to clone a lactate dehydrogenase gene of *Klebsiella oxytoca*, a homologous site 1 (SEQ ID NO: 2) of a target gene ldhA (SEQ ID NO: 1) was amplified using primers of SEQ ID NOs: 3 and 4 by polymerase chain reaction (PCR). Further, a homologous site 2 (SEQ ID NO: 5) was amplified using primers of SEQ ID NOs: 6 and 7 by PCR. Next, the homologous sites 1 and 2 were amplified using the same as templates for PCR, thereby obtaining a completed DNA fragment (SEQ ID NO: 8) in which the homologous sites 1 and 2 were ligated. The completed DNA fragment may include antibiotic resistance genes and the like in order to enhance the probability of recombination of target genes. Further, the completed DNA fragment may include a sacB gene encoding levansucrase enzyme in order to remove antibiotic resistance genes recombined in the chromosomes.

The prepared DNA fragment was transferred to wild type *Klebsiella oxytoca* through electroporation (25 uF, 200 Ω, 18 kV/cm), in which the target gene is deleted by means of an innate homologous recombination mechanism.

TABLE 1

| SEQ ID NO: | Sequence |
|---|---|
| 1 | ATGAAAATCGCTGTGTATAGTACAAAACAGTACGACAAGAAGTATCTGCAGCATGTTAATGATGCAT<br>ATGGCTTTGAACTGGAGTTTTTTGACTTCCTGCTAACCGAAAAAACCGCCAAAACCGCCAACGGCTG<br>TGAAGCGGTGTGTATCTTCGTAAACGATGACGGTAGCCGCCCGGTACTTGAAGAACTGAAAGCCCAC<br>GGCGTGCAGTACATCGCGCTGCGCTGCGCGGGGTTCAACAACGTTGACCTCGATGCCGCCAAAGAGC<br>TGGGCCTGCGGGTGGTGCGCGTCCCGGCCTACTCGCCGGAAGCGGTCGCTGAGCACGCGATCGGCAT<br>GATGATGTCGCTGAACCGCCGCATTCACCGTGCCTATCAGCGCACCCGCGACGCGAACTTCTCTCTG<br>GAAGGGCTGACCGGTTTCACCATGCACGGTAAAACCGCCGGCGTTATTGGCACCGGTAAAATCGGCG<br>TCGCCGCGCTGCGCATTCTTAAAGGCTTCGGTATGCGTCTGCTGGCGTTTGATCCCTACCCAAGCGC<br>CGCCGCGCTGGATATGGGCGTGGAGTATGTCGATCTTGAAACCCTGTACCGGGAGTCCGATGTTATC<br>TCACTGCACTGCCCACTGACCGATGAAAACTACCATTTGCTGAACCATGCCGCGTTCGATCGCATGA<br>AAGACGGGGTGATGATCATCAACACCAGCCGCGGCGCGCTCATCGATTCGCAGGCAGCGATCGACGC<br>CTGAAGCATCAGAAAATTGGCGCGCTGGGGATGGACGTGTATGAGAACGAACGCGATCTGTTCTTTG<br>AGATAAGTCTAATGACGTGATTCAGGATGATGTGTTCCGCCGTCTCTCCGCCTGCCATAACGTCCTG<br>TTTACCGGTCACCAGGCGTTTCTGACCGCGGAAGCGTTGATCAGCATTTCGCAAACCACCCTCGACA<br>ACCTGCGTCAAGTGGATGCAGGCGAAACCTGTCCTAACGCACTGGTCTGA |

TABLE 1-continued

| SEQ ID NO: | Sequence |
|---|---|
| 2 | ATGACGTTCGCTAAATCCTGCGCCGTCATCTCGCTGCTGATCCCGGGCACCTCCGGGCTACTGCTGT<br>TCGGCACCCTGGCATCGGCCAGCCCGGGACATTTCCTGTTAATGTGGATGAGCGCCAGCCTCGGCGC<br>TATCGGCGGATTCTGGCTCTCGTGGCTGACGGGCTACCGCTACCGGTACCATCTGCATCGTATCCGC<br>TGGCTTAATGCCGAACGCCTCGCTCGCGGCCAGTTGTTCCTGCGCCGCCACGGCGCGTGGGCAGTCT<br>TTTTTAGCCGCTTTCTCTCTCCGCTTCGCGCCACCGTGCCGCTGGTAACCGGCGCCAGCGGCACCTC<br>TCTCTGGCAGTTTCAGCTCGCCAACGTCAGCTCCGGGCTGCTCTGGCCGCTGATCCTGCTGGCGCCA<br>GGCGCGTTAAGCCTCAGCTTTTGATGAAAGGTATTGTCTTTTAAAGAGATTTCTTAACACCGCGATA<br>TGCTCTAGAATTATTACTATAACCTGCTGATTAAACTAGTTTTTAACATTTGTAAGATTATTTTAAT<br>TATGCTACCGTGACGGTATTATCACTGGAGAAAAGTCTTTTTTCCTTGCCCTTTTGTGC |
| 3 | Ko.jdh.FP1-CACGGATCCATGACGTTCGCTAAATCCTGC |
| 4 | Ko_IdhA_RP1-GCACAAAAGGGCAAGGAAAAAAGACTTTTCTCCAGTGATA |
| 5 | TATCACTGGAGAAAAGTCTTTTTTCCTTGCCCTTTTGTGCTCCCCCTTCGCGGGGGGCACATTCAGA<br>TAATCCCCACAGAAATTGCCTGCGATAAAGTTACAATCCCTTCATTTATTAATACGATAAATATTTA<br>TGGAGATTAAATGAACAAGTATGCTGCGCTGCTGGCGGTGGGAATGTTGCTATCGGGCTGCGTTTAT<br>AACAGCAAGGTGTCGACCAGAGCGGAACAGCTTCAGCACCACCGTTTTGTGCTGACCAGCGTTAACG<br>GGCAGCCGCTGAATGCCGCGGATAAGCCGCAGGAGCTGAGCTTCGGCGAAAAGATGCCCATTACGGG<br>CAAGATGTCTGTTTCAGGTAATATGTGCAACCGCTTCAGCGGCACGGGCAAAGTCTCTGACGGCGAG<br>CTGAAGGTTGAAGAGCTGGCAATGACCCGCATGCTCTGCACGGACTCGCAGCTTAACGCCCTGGACG<br>CCACGCTGAGCAAAATGCTGCGCGAAGGCGCGCAGGTCGACCTGACGGAAACGCAGCTAACGCTGGC<br>GACCGCCGACCAGACGCTGGTGTATAAGCTCGCCGACCTGATGAATTAATAATTA |
| 6 | Ko_IdhA_FP2-TATCACTGGAGAAAAGTCTTTTTTCCTTGCCCTTTTGTGTC |
| 7 | Ko_IdhA_RP2-CCTGCGGCCGCTAATTATTAATTCATCAGGTC |
| 8 | ATGACGTTCGCTAAATCCTGCGCCGTCATCTCGCTGCTGATCCCGGGCACCTCCGGGCTACTGCTGT<br>TCGGCACCCTGGCATCGGCCAGCCCGGGACATTTCCTGTTAATGTGGATGAGCGCCAGCCTCGGCGC<br>TATCGGCGGATTCTGGCTCTCGTGGCTGACGGGCTACCGCTACCGGTACCATCTGCATCGTATCCGC<br>TGGCTTAATGCCGAACGCCTCGCTCGCGGCCAGTTGTTCCTGCGCCGCCACGGCGCGTGGGCAGTCT<br>TTTTTAGCCGCTTTCTCTCTCCGCTTCGCGCCACCGTGCCGCTGGTAACCGGCGCCAGCGGCACCTC<br>TCTCTGGCAGTTTCAGCTCGCCAACGTCAGCTCCGGGCTGCTCTGGCCGCTGATCCTGCTGGCGCCA<br>GGCGCGTTAAGCCTCAGCTTTTTGATGAAAGGTATTGTCTTTTAAAGAGATTTCTTAACACCGCGAT<br>ATGCTCTAGAATTATTACTATAACCTGCTGATTAAACTAGTTTTTAACATTTGTAAGATTATTTTAA<br>TTATGCTACCGTGACGGTATTATCACTGGAGAAAAGTCTTTTTTCCTTGCCCTTTTGTGCTCCCCCT<br>TCGCGGGGGGCACATTCAGATAATCCCCACAGAAATTGCCTGCGATAAAGTTACAATCCCTTCATTT<br>ATTAATACGATAAATATTTATGGAGATTAAATGAACAAGTATGCTGCGCTGCTGGCGGTGGGAATGT<br>TGCTATCGGGCTGCGTTTATAACAGCAAGGTGTCGACCAGAGCGGAACAGCTTCAGCACCACCGTTT<br>TGTGCTGACCAGCGTTAACGGGCAGCCGCTGAATGCCGCGGATAAGCCGCAGGAGCTGAGCTTCGGC<br>GAAAAGATGCCCATTACGGGCAAGATGTCTGTTTCAGGTAATATGTGCAACCGCTTCAGCGGCACGG<br>GCAAAGTCTCTGACGGCGAGCTGAAGGTTGAAGAGCTGGCAATGACCCGCATGCTCTGCACGGACTC<br>GCAGCTTAACGCCCTGGACGCCACGCTGAGCAAAATGCTGCGCGAAGGCGCGCAGGTCGACCTGACG<br>GAAACGCAGCTAACGCTGGCGACCGCCGACCAGACGCTGGTGTATAAGCTCGCCGACCTGATGAATT<br>AATAATTA |

EXPERIMENTAL EXAMPLE 1

2,3-butanediol Conversion Enzyme

Figure 2:
FIG. 2 shows an operon of a 2,3-butanediol synthesis related gene in *Klebsiella oxytoca*.

Enzymes related to 2,3-butanediol synthesis and consumption pathways were screened using KEGG database (http://www.genome.jp/kegg/) and NCBI database ((http://www.ncbi.nlm.nih.gov/blast/) based on genome information of *Klebsiella oxytoca* KCTC 12133BP. As a result, it was confirmed that all species belonging to *Klebsiella oxytoca*, genome information of which is known, have at least two 2,3-butanediol conversion enzymes (AR1 and AR2). FIG. 2 shows a schematic diagram of a gene group based on the above-mentioned matters.

The amino acid sequence of AR1 is set forth in SEQ ID NO: 9, and the nucleotide sequence of budC which encodes AR1 is set forth in SEQ ID NO: 10. Meanwhile, the amino acid sequence of AR2 is set forth in SEQ ID NO: 11, and the nucleotide sequence of dar which encodes AR2 is set forth in SEQ ID NO: 12 (see Table 2).

TABLE 2

| SEQ ID NO: | Sequence |
|---|---|
| 9 | MKKVALVTGAGQGTGKATALRLVKDGFAVATADYNDATAQAVADENRSGGRALAVKVDVSQR<br>DQVFAAVEQARKGLGGFDVIVNNAGVAPSTPIEETREEVIDKVYNNVKGVIWGTQAAVEAFK<br>KEGHGGKIINACSQAGHVGNPELAVYSSSKFAVRGLTQTAARDLAHLGITVNGYCPGIVKTP<br>MWAEIDRQVSEAAGKPLGYGTQEFAKRITLGRLSEPEDVAACVSYLAGPDSNVMTGQSLLEN<br>DGGMVFN |
| 10 | ATGAAAAAGTCGCACTCGTCACCGGCGCGGGCCAGGGTATCGGTAAAGCTATCGCCCTTCG<br>TCTGGTGAAAGATGGTTTTGCCGTGGCTATCGCCGATTATAACGACGCCACCGCGCAGGCGG<br>TCGCTGATGAAATTAACCGCAGCGGCGGCCGGGCGCTACGGTGAAGGTGGATGTGTCTCAAC |

TABLE 2-continued

| SEQ ID NO: | Sequence |
|---|---|
| | GCGATCAGGTTTTTGCCGCCGTCGAACAGGCGCGCAAGGGTCTCGGCGGTTTTGACGTGATC<br>GTCAACAACGCCGGGGTTGCGCCCTCCACACCAATCGAAGAGATTCGCGAGGAGGTGATCGA<br>TAAAGTCTACAATATCAACGTTAAAGGCGTTATCTGGGGCATCCAGGCCGCGGTAGAGGCGT<br>TTAAAAAAGAGGGCCACGGCGGCAAAATTATCAACGCCTGCTCCCAGGCGGGCCATGTAGGT<br>AACCCGGAGCTGGCGGTCTATAGCTCCAGTAAATTTGCCGTGCGCGGCCTGACGCAAACCGC<br>GCCCGCGATCTGGCGCATCTGGGATTACCGTAAACGGCTACTGCCCGGGGATCGTCAAAACC<br>CCAATGTGGGCGGAAATTGACCGCCAGGTTTCCGAAGCGGCGGGTAAACCGCTGGGCTACGG<br>AACCCAGGAGTTCGCCAAACGCATTACCCTTGGGCGGCTATCCGAGCCGGAAGACGTCGCAG<br>CCTGCGTCTCTTATCTCGCCGGTCCGGACTCCAATTATATGACCGGCCAATCGCTGCTGATC<br>GATGGCGGCATGGTATTTAAC |
| 11 | MAIENKVALVTGAGQGIGRGIALRLAKDGASVMLVDVNPEGIAAVAAEVEALGRKAATFVAN<br>TADRAQVYAAIDEAEKQLGGFDIIVNNAGIAQVQALADVTPEEVDRIMRINVQGTLWGIQAA<br>AKKMDRQQKGKIINACSIAGHDGFALLGVYSAIKFAVRALTQAAAKEYASRGITVNAYCPGI<br>VGTGMWTEIDKRFABTGAPVGETYKKYVEGTALGRAETPDDVASLVSYLAGPDSDVVTGQSL<br>IDGGIVYR |
| 12 | ATGGCTATCGAAAATAAAGTTGCGCTGGTAACCGGCGCCGGTCAGGGCATTGGCCGCGGTAT<br>TGCGTTGCGTCTGGCCAAAGACGGCGCGTCGGTGATGCTGGTCGACGTGAACCCTGAAGGGA<br>TTGCCGCCGTCGCCGCCGAAGTGGAAGCGCTGGGACGCAAAGCAGCCACCTTCGTCGCTAAC<br>ATCGCCGATCGCGCGCAGGTGTACGCCGCCATTGATGAAGCGAAAAACAGCTGGGCGGCTTT<br>GATATTATCGTGAACAACGCCGGGATCGCCCAGGTTCAGGCGCTGGCCGATGTGACGCCTGA<br>AGAAGTGGACCGCATCATGCGCATCAACGTTCAGGGTACCCTGTGGGGTATTCAGGCGGCGG<br>CGAAAAAATTCATCGATCGTCAGCAGAAAGGGAAAATCATCAACGCCTGCTCTATCGCCGGT<br>CATGATGGTTTCGCGCTGCTGGGCGTTTATTCCGCCACCAAATTTGCCGTACGCGCCCTGAC<br>GCAGGCGGCGGCGAAGGAGTATGCCAGCCGCGGCATTACGGTTAATGCCTACTGTCCGGGGA<br>TTGTGGGAACCGGGATGTGGACCGAAATCGATAAGCGCTTTGCGGAAATTACCGGTGCGCCG<br>GTGGGCGAAACTTATAAAAAATACGTTGAAGGCATCGCCCTTGGCCGCGCCGAAACGCCGGA<br>CGATGTGGCAAGCCTGGTCTCTTATCTGGCAGGCCCGGATTCCGATTATGTTACCGGTCAGT<br>CGATTCTGATCGATGGCGGATATTGTTTACCGT |

To date, 2,3-butanediol producing microorganisms including genus *Klebsiella* microorganisms are known to have one 2,3-butanediol conversion enzyme. Furthermore, in general genus *Klebsiella* microorganisms, the 2,3-butanediol conversion enzymes corresponding to AR1 exist as an operon with related enzymes (ALDC and ALS) (Oppermann, U. et al., Chem. Biol. Interact. 143: 247-253). Namely, AR2 identified in the present invention is a novel enzyme which has not been previously known in the art, and AR2 is characterized by having properties as set forth in the following (1) to (3):

1) 2,3-butanediol conversion enzyme belongs to the short-chain dehydrogenases/reductases (SDR) family SDR is characterized by having 250 to 350 amino acid residues.

2) 2,3-butanediol conversion enzyme has binding sites for NADH which is coenzyme at its N-terminal (Glycine-rich TGXXXGXG (SEQ ID No: 27) and NNAG motifs).

3) 2,3-butanediol conversion enzyme has a catalytic tetrad Asn-Ser-Tyr-Lys amino acid residues (SEQ ID No:28) and an active site YXXXK (SEQ ID No:29).

EXPERIMENTAL EXAMPLE 2

Identification of 2,3-butanediol Conversion Enzyme

Figure 3:
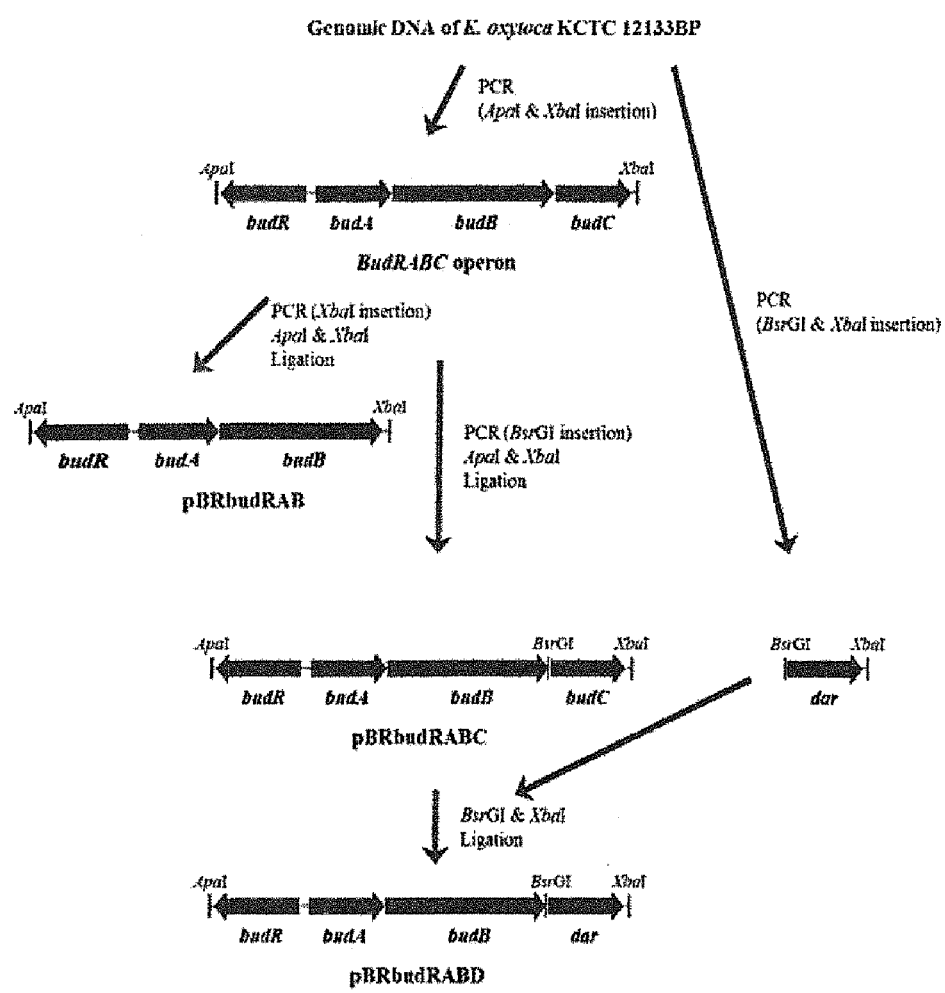
FIG. 3 shows a schematic view of construction of recombinant vectors for expression in *Escherichia coli* (*E. coli* JM109) to identify cellular functions of 2,3-butanediol synthesis related genes found in *Klebsiella oxytoca*.

In order to experimentally identify 2,3-butanediol conversion activity of AR1 and AR2, a recombinant plasmid depicted in FIG. 3 was constructed. pBBR1MCS containing a chloramphenicol resistance gene was utilized as a basic vector (Kovach, M. E., et al., Biotechniques 16: 800-802).

pBRbudRAB contains a transactivator (TA) gene, an acetolactate synthase (ALS) gene, and an acetoin dicarboxylase (ALDC) gene, and is expected to ensure acetoin synthesis. pBRbudRABC contains a transactivator (TA) gene, an acetolactate synthase (ALS) gene, an acetoin dicarboxylase (ALDC) gene, and a 2,3-butanediol conversion enzyme (AR1) gene, and is expected to ensure production of 2,3-butanediol. Meanwhile, pBRbudRABD contains a transactivator (TA) gene, an acetolactate synthase (ALS) gene, an acetoin dicarboxylase (ALDC) gene, and a 2,3-butanediol conversion enzyme (AR2) gene, and thus production of 2,3-butanediol is dependent on functions of AR2.

*Escherichia coli* (*E. coli* JM109) was transformed with the above constructed plasmids, thereby obtaining recombinant *Escherichia coli*. The recombinant *Escherichia coli* were used to perform fermentation. In order to maintain the recombinant vectors introduced in all cultivation procedures, chloramphenicol was added in a concentration of 30 µg/ml. The fermentation was performed by plating the recombinant *Escherichia coli* onto a 250 ml composite medium including 9 g/L glucose (50 mM, glucose), culturing the recombinant *Escherichia coli* at 37° C. for 16 hours and plating the resulting culture solution onto 3 L of a composite medium. The fermentation conditions were as follows: microaerobic conditions; aerobic speed of 1 vvm, stirring rate of 400 rpm), 90 g/L of initial glucose concentration, pH 6.8, a culture temperature of 37° C. Upon fermentation, 5N NaOH was used to adjust pH. Samples were taken during fermentation using the recombinant *Escherichia coli*. The growth rate was determined by measuring OD600 (optical density) of the samples. The sampled specimens were subjected to centrifugation at 13,000 rpm for 10 minutes, followed by assaying the concentration of metabolites and 2,3-butanediol in the supernatant through high performance liquid chromatography (HPLC).

Figure 4:
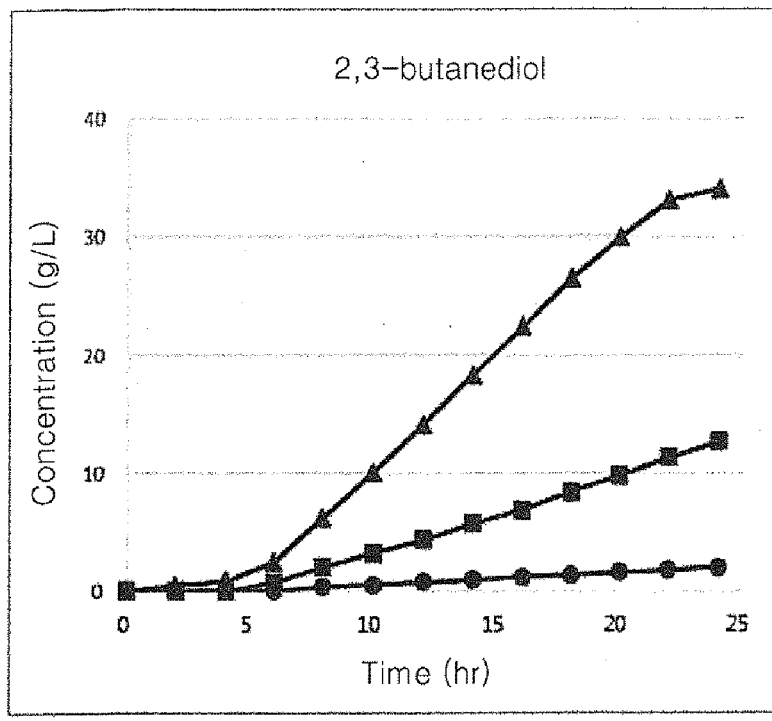
FIG. 4 shows the ability to produce 2,3-butanediol upon batch fermentation of the recombinant *Escherichia coli*.
Figure 5:
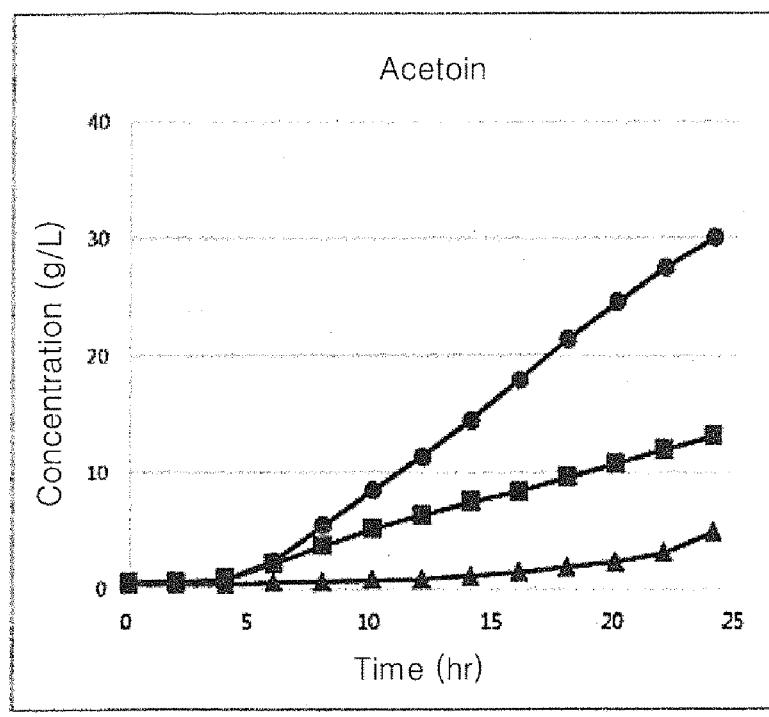
FIG. 5 shows the ability to produce acetoin upon batch fermentation of the recombinant *Escherichia coli* (●: pBRbudRAB/*E. coli* JM109, ▲: pBRbudRABC/*E. coli* JM109, ■: pBRbudRABD/*E. coli* JM109).

As a result, after 24 hours of fermentation, pBRbudRAB/*E. coli* JM109 was found to produce 2.0 g/L of 2,3-butanediol and 30.0 g/L of acetoin. On the contrary, pBRbudRABC/*E. coli* JM109 was found to produce 34.0 g/L of 2,3-butanediol and 4.7 g/L of acetoin. pBRbudRABD/*E. coli* JM109 was found to produce 12.6 g/L of 2,3-butanediol and 13.0 g/L of acetoin (FIG. 4: 2,3-butanediol production ability and FIG. 5: acetoin production ability. ■: pBR-budRAB/*E. coli* JM109, ▲: pBRbudRABC/*E. coli* JM109, ■: pBRbudRABD/*E. coli* JM109).

In other words, it was confirmed that the recombinant strain containing dar encoding AR2 also ensures production of 2,3-butanediol, although the ability to synthesize 2,3-butanediol is inferior to that of the recombinant strain containing budC gene encoding AR1. Therefore, it can be seen that both AR1 and AR2 were enzymes having conversion activity of 2,3-butanediol.

EXPERIMENTAL EXAMPLE 3

Construction of Recombinant Strains with Deleted AR1 and AR2

In order to perform deletion of genes encoding AR1 (encoded by budC gene) and AR2 (encoded by dar gene) which were found to be 2,3-butanediol conversion enzymes in Experimental Example 2 from the genome of *Klebsiella oxytoca*, a homologous recombination mechanism of microorganisms was employed. The recombinant DNA fragment to inactivate the target gene of *Klebsiella oxytoca* includes a homologous region to the gene to be deleted, and a sacB gene encoding levansucrase enzyme to remove antibiotic resistance genes recombed in the chromosome so that the recombination probability is enhanced. If the constructed DNA fragment is introduced to a target microorganism (*Klebsiella oxytoca*), the targeted gene is removed through a recombinant mechanism between homologous regions of a gene in the DNA fragment and a gene in microorganism genome by a recombinase.

A recombinant plasmid for the deletion of AR1 (budC) gene and AR2 (dar) gene of *Klebsiella oxytoca* was constructed in the manner as mentioned below.

Firstly, in order to delete AR1, a homologous region 1 (SEQ ID NO: 13) of the target gene budC (SEQ ID NO: 10) was amplified by PCR using primers of SEQ ID NOs: 14 and 15. A homologous region 2 (SEQ ID NO: 16) was amplified by PCR using primers of SEQ ID NOs: 17 and 18. Subsequently, at the same time, the homologous regions 1 (SEQ ID NO: 13) and 2 (SEQ ID NO: 16) were used as templates for PCR amplification, thereby obtaining a DNA fragment (SEQ ID NO: 19) in which the homologous regions 1 and 2 were ligated (Table 3).

TABLE 3

| SEQ ID NO: | Sequence |
|---|---|
| 13 | GCTGCGCATCGTTCGCGCCATGCAGGACATCGTCAATAGCGATGTCACCCTGACCGTCGATATGGG GAGCTTTCATATCTGGATCGCCCGCTATCTCTACAGCTTTCGCGCCCGTCAGGTCATGATTTCCAA CGGTCAACAGACCATGGGCGTGCGCTGCCGTGGGCGATTGGCGCCTGGCTGGTCAATCCGCAGCGC AAAGTGGTTTCCGTTTCCGGCGACGGCGGTTTCCTGCAGTCCAGCATGGAGCTGGAGACCGCTGTA CGGCTGAAAGCGAACGTCCTGCATATCATCTGGGTCGATAACGGCTACAACATGGTGGCGATTCAG GAGGAGAAAAAATACCAGCGGCTCTCCGGCGTTGAGTTCGGCCCGGTGGATTTTAAAGTCTACGCC GAAGCCTTCGGCGCCAAAGGGTTTGCGGTAGAGAGCGCCGAAGCCCTTGAGCCGACGCTGCGGGCG GCGATGGACGTCGACGGCCCCGCCGTCGTAGCCATCCCCGTGGATTACCGCGATAACCCGCTGCTG ATGGGCCAGCTCCATCTCAGTCAACTACTTTGAGTCACTACAGAAGGAATCTATCAATGAAAAAAG TCGCACTCGTGACCGGCGCGATGACCGGCCAATCGCTGCTGATCG |
| 14 | GGATCCGCTGCGCATCGTTCGCGCCATGC |
| 15 | CGATCAGCAGCGATTGGCCGGTCATCGCCCCGGTCACGAGTGCGACTT |
| 16 | AAGTCGCACTCGTGACCGGCGCGATGACCGGCCAATCGCTGCTGATCGATGGCGGCATGGTATTTA ACTAATAATAAATAAGCTCTGACATGGTTTGCCCCGGCGTCACCGCCGGGGCTTTTTTATTTCAAC CTTTAGGGAAGATCCACAGGTCGCTGACGGGCAATGTCAGATGGCAACGCTCGGCATCGCGCAGCG CGCTGCCGTAGGCGCGTATGGCGAAATCATCGCCTTCAGTGCGAAACAGATACTCCCAGCGGTCGC CGAGGTACATGCTGGTCAACAGCGGCAGCGCCAGCATGTTCTCTTCAGGCGCGGAAGCGATGCGCA AACGCTCAACGCGGATCACCGCCGTCGCCTCTTCCCCACGCTAACCCCTTCCCCGCCATTCCCATA GCGCCCAGCTGGCCCCTCAATGCGCGCCCGACCGTTCTCCAGCGCGCTAACGGTGCCATGCAGGCG ATTATTACTGCCCATAAACTCGGCGGCAAACAGCGTTTTCGGGCTGCCGTACATCTCCTGCGGGGT TCCCTGCTGCTCGATCACGCCGTTGTTAAGCAGCAGAATGCGATCGGAAATCGCCATCGCCTCGTT CTGATCGT |
| 17 | AAGTCGCACTCGTGACCGGCGCGATGACCGGCCAATCGCTGCTGATCG |
| 18 | GCGGCCGCACGATCAGAACGAGGCGATGGCGAT |
| 19 | GCTGCGCATCGTTCGCGCCATGCAGGACATCGTCAATAGCGATGTCACCCTGACCGTCGATATGGG GAGCTTTCATATCTGGATCGCCCGCTATCTCTACAGCTTTCGCGCCCGTCAGGTCATGATTTCCAA CGGTCAACAGACCATGGGCGTGGCGCTGCCGTGGGCGATTGGCGCCTGGCTGGTCAATCCGCAGCG CAAAGTGGTTTCCGTTTCCGGCGACGGCGGTTTCCTGCAGTCCAGCATGGAGCTGGAGACCGCTGT ACGGCTGAAAGCGAACGTCCTGCATATCATCTGGGTCGATAACGGCTACAACATGGTGGCGATTCA GGAGGAGAAAAAATACCAGCGGCTCTCCGGCGTTGAGTTCGGCCCGGTGGATTTTAAAGTCTACGC CGAAAGCCTTCGGCGCCAAAGGGTTTGCGGTAGAGAGCGCCGAAGCCCTTGAGCCGACGCTGCGGG CGGCGATGGACGTCGACGGCCCCGCCGTCGTAGCCATCCCCGTGGATTACCGCGATAACCCGCTGC TGATGGGCCAGCTCCATCTCAGTCAACTACTTTGAGTCACTACAGAAGGAATCTATCAATGAAAAA AGTCGCACTCGTGACCGGCGCGATGACCGGCCAATCGCTGCTGATCGATGGCGGCATGGTATTTAA CTAATAATAAATAAGCTCTGACATGGTTTGCCCCGGCGTCACCGCCGGGGCTTTTTTATTTCAACC TTTAGGGAAGATCCACAGGTCGCTGACGGGCAATGTCAGATGGCAACGCTCGGCATCGCGCAGCGG CTGCCGTAGGCGCGTATGGCGAAATCATCGCCTTCAGTGCGAAACAGATACTCCCAGCGGTCGCC GAGGTACATGCTGGTCAACAGCGGCAGCGCCAGCATGTTCTCTTCAGGCGCGGAAGCGATGCGCAA ACGCTCAACGCGGATCACCGCCGTCGCCTCTTCCCCCACGCTAACCCCTTCCCCCATTCCCCATAG CGGCCAGCTGGCCCCCTCAATGCGCGCCCGACCGTTCTCCAGCGCGCTAACGGTGCCATGCAGGCG ATTATTACTGCCCATAAACTCGGCGGCAAACAGCGTTTTCGGGCTGCCGTACATCTCCTGCGGGGT |

TABLE 3-continued

| SEQ ID NO: | Sequence |
|---|---|
| | TCCCTGCTGCTCGATCACGCCGTTGTTAAGCAGCAGAATGCGATCGGAAATCGCCATCGCCTCGTTCTGATCGT |

In addition, in order to delete AR2, a homologous region 1 (SEQ ID NO: 20) of the target dar gene (SEQ ID NO: 12) was amplified by PCR using primers of SEQ ID NOs: 21 and 22. A homologous region 2 (SEQ ID NO: 23) was amplified by PCR using primers of SEQ ID NOs: 24 and 25. Subsequently, at the same time, the homologous regions 1 (SEQ ID NO: 20) and 2 (SEQ ID NO: 23) were used as templates for PCR amplification, thereby obtaining a DNA fragment (SEQ ID NO: 26) in which the homologous regions 1 and 2 were ligated (Table 4).

TABLE 4

| SEQ ID NO: | Sequence |
|---|---|
| 20 | GGAGGTCGGCCGGAAGCTCGCCTTGCAGCAGCTGCAGAAACGACGGGCTCCACCCCTGCCACAAG GGCCGCAGCGCCTCCTGCAGATAGCGTATAAACAGTAGCGGCGCGTTGTCATCCTCTTCAAGGCT CAGCCAGGCCAGCGCATCCCCTTGTCGAAGGCGGTGTCGATACCACTGCGCCAGCAGGGTGGTTT TGCCAAATCCGGCGGGCGCGCGCACCAGGGTTAAACGGCGGGAGACGGCGGCGTCGAGGCGCTGT AGCAGGCGCTCCCGCGATAGCAGACTTTCCGGCGTACGGGGCGGCGTAAAGCGCGTGGAGATAAG CGGCAGCGTCCCCGTGAAGCGTAAAGGTTCCTGATGAACAAGCGCTGCCAGCGCATCATCCGCCG AGGATAAAAAGGCCATACCACGATTACTCCTTAATCCAGTCCGTACGCTCATTATCCCCCCCATC AGGGGGGTAGGCCACGCTTATCGCGCCCGATAGAGTAGTGCCATTCGCCGCAGCGGCTACGACGA CATCGGCCGCGGGCCTCCCTAGTTTATTAATCAGTACAAGGTGAGTACAGACATGGCTATCGAAA ATAAAGTTGCGACCGGTCAGTCGATTCTGATCGATG |
| 21 | TCTAGAGGATCCGGAGGTCGGCCGGAAGCTCGCC |
| 22 | CATCGATCAGAATCGACTGACCGGTCGCAACTTATTTTCGATAGCCATGTC |
| 23 | GACATGGCTATCGAAAATAAAGTTGCGACCGGTCAGTCGATTCTGATCGATGGCGGTATTGTTTA CCGTTAAGGGATAAACCCGGCGCAGAACGCGCCGGGTTTTTGCGGGGTTACGCGTTAGCCGCGGG CTCCTGCGGCTTGTCGCTACGGGTGTTTTCCAGCATCCGGCGAACCGGAACAATCAGCAGGCACA GCACCGCGGCGCAGATCAGCAGCGCAATAGAGCAGCGTCGAACAGGTCGGGCAGCATATCCAGCT GATCGGCCTTCACGTGACCGCCAATCAGACCCGCCGCCAGGTTCCCCAGGGCGCTGGCGCAGAAC CACAGCCCCATCATCGGCCGCGCATTCTTTCCGGCGCCAGCAGCGTCATGGTCGCGAGGCCAAT CGGGCTGAGGCACAGCTCGCCCAGCGTCAGCATCAGAATACTGCCCACCAGCCACATCGGCGAGA CGCCCGCGCCGTTGTTGCTCAGGACGTTTTGCGCCGCCAGCATCATCAGGCCAAAGCCCGCCGCC GCGCATAAAATACCGATAACAAACTGGTGATGCTGCTCGGACGCACGTTTTTACGCGCCAGCGCA GGCCACGCCCAGCTAAATACC |
| 24 | GACATGGCTATCGAAAATAAAGTTGCAGACCGGTCAGTCGATTCTGATCGATG |
| 25 | ATCGCGGCCGCGGTATTTAGCTGGGCGTGGCCTGC |
| 26 | GGAGGTCGGCCCGGAAGCTCGCCTTGCAGCAGCTGCAGAAACGACGGGCTCCACCCCTGCCACAA GGGCCGCAGCGCCTCCTGCAGATAGCGTATAAACAGTAGCGGCGCGTTGTCATCCTCTTCAAGGC TCAGCCAGGCCAGCGCATCCCCTTGTCGAAGGCGGTGTCGATACCACTGCGCCAGCAGGTGGTTT TGCCAAATCCGGCGGGCGCGCACCAGGGTTAAACGGCGGGAGACGGCGGCGTCGAGGCGCTGT AGCAGGCGCTCCCGCGATAGCAGACTTTCCGGCGTACGGGGCGGCGTAAAGCGCGTGGAGATAAG CGGCAGCGTCCCCGTGAAGCGTAAAGGTTCCTGATGAACAAGCGCTGCCAGCGCATCATCCGCCG AGGATAAAAAGGCCATACCACGATTACTCCTTAATCCAGTCCGTACGCTCATTATCCCCCCCATC AGGGGGGTAGGCCACGCTTATCGCGCCCGATAGAGTAGTGCCATTCGCCGCAGCGGCTACGACGA CATCGGCCGCGGGCCTCCCTAGTTTATTAATCAGTACAAGGTGAGTACAGACATGGCTATCGAAA ATAAAGTTGCGACCGGTCAGTCGATTCTGATCGATGGCGGTATTGTTTACCGTTAAGGGATAAAC CCGGCGCAGAACGCGCCGGGTTTTTGCGGGGTTACGCGTTAGCCGCGGGCTCCTGCGGCTTGTCG CTACGGGTGTTTTCCAGCATCCGGCGAACCGGAACAATCAGCAGGCACAGCACCGCGGCGCAGAT CAGCAGCGCAATAGAGCAGCGTGCGAACAGGTCGGGCAGCATATCCAGCTGATCGGCCTTCACGT GACCGCCAATCAGACCCGCCGCCAGGTTCCCCAGGGCGCTGGCGCAGAACACAGCCCCATCATC TGGCCGCGCATTCTTTCCGGCGCCAGCAGCGTCATGGTCGCGAGGCCAATCGGGCTGAGGCACAG CTCGCCCAGCGTCAGCATCAGAATACTGCCCACCAGCCACATCGGCAGAGACGCCCGCGCCGTTG TTGCTCAGGACGTTTTGCGCCGCCAGCATCATCAGGCCAAAGCCCGCCGCCGCGCATAAAATACC GATAACAAACTGGTGATGCTGCTCGGACGCACGTTTTACGCGCCAGCGCAGGCCACGCCCAGCT AAATACC |

*Klebsiella oxytoca* KCTC 12133BP ΔldhA (KO ΔldhA) in which a gene encoding lactate dehydrogenase (ldhA) was deleted was prepared. DNA fragments of SEQ ID NOs: 19 and 26 were introduced to *Klebsiella oxytoca* (KO ΔldhA) by means of electroporation (25 uF, 200 Ω, 18 kV/cm), respectively. Accordingly, a recombinant strain (KO ΔldhA ΔbudC) in which the gene AR1 (budC) was removed from KO ΔldhA, and a recombinant strain (KO ΔldhA Δdar) in which the gene AR2 (dar) was removed from KO ΔldhA were constructed, respectively.

Furthermore, a pKOV deltaAR2 plasmid was introduced to the recombinant strain (KO ΔldhA ΔbudC) in which AR1 (budC) was deleted, thereby obtaining a recombinant strain (KO ΔldhA ΔbudC Δdar) in which AR2 (dar) gene was further deleted.

The general procedures for deleting genes after the introduction of the DNA fragments include antibiotic resistance tests and sucrose resistance tests, and the deletion of corresponding genes was confirmed by performing colony PCR.

EXPERIMENTAL EXAMPLE 4

Examination on the Functions of AR1 and AR2

The functions of AR1 and AR2 proteins were examined by the consumption pathway of 2,3-butanediol using acetoin as an intermediate. Specifically, growth of the recombinant strains of *Klebsiella oxytoca* and residual 2,3-butanediol concentration were observed using 2,3-butanediol as a sole carbon source in M9 minimum medium. The strains were streaked onto LB solid medium, followed by culturing at 30° C. for 16 hours, and then culturing the single colonies in 3 ml of LB liquid medium for 8 hours. The culture solution was washed with M9 minimum medium twice to remove the residual LB components. 100 ml M9 basic medium containing 10 g/L 2,3-butanediol was inoculated with the resulting solution, and then cultured. Samples were taken while culturing the recombinant strains. The sampled specimens were subjected to OD600 (optical density) measurement, thereby determining the growth rate. The sampled specimens were subjected to centrifugation at 13,000 rpm for 10 minutes. The concentration of metabolites and 2,3-butanediol in the supernatant was assayed by high performance liquid chromatography (HPLC).

Figure 6:
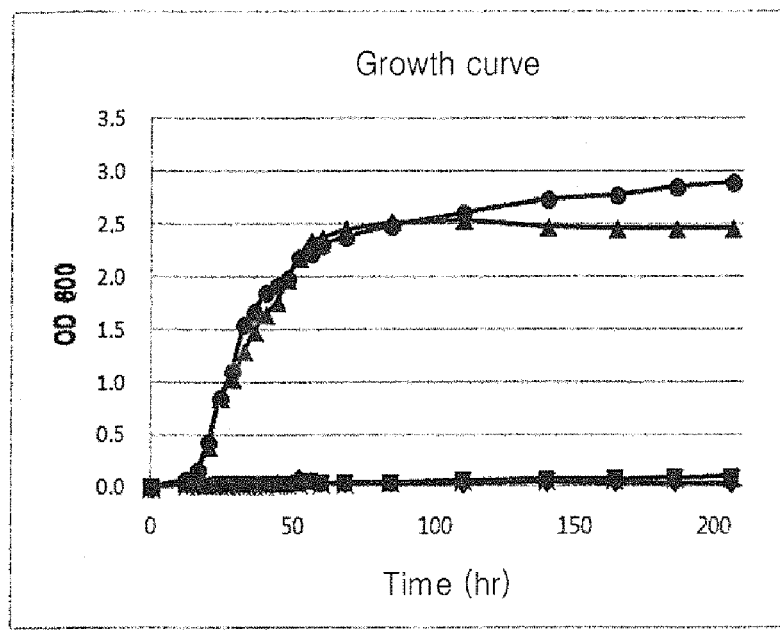
FIG. 6 shows a growth curve of the recombinant strains of *Klebsiella* grown in M9 minimal medium using 2,3-butanediol as a sole carbon source.
Figure 7:
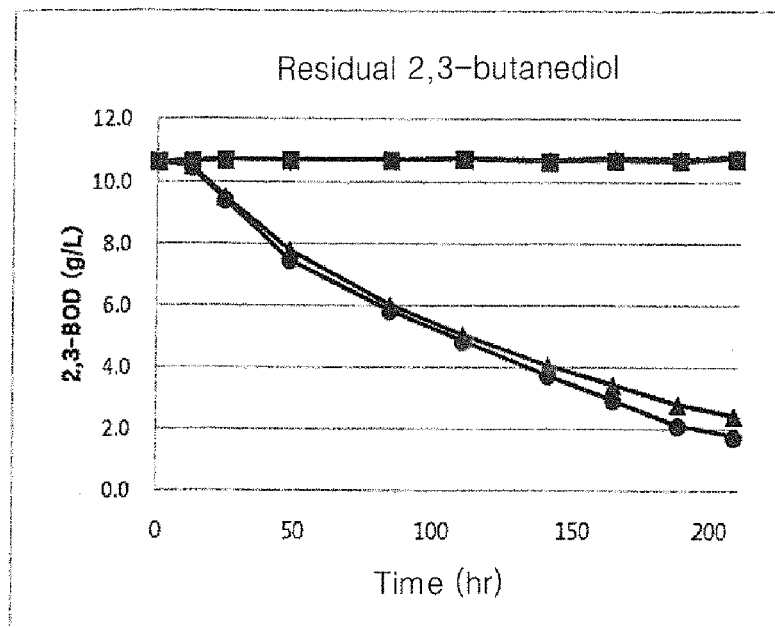
FIG. 7 shows a concentration of residual 2,3-butanediol when the recombinant strains of *Klebsiella* are grown in M9 minimal medium using 2,3-butanediol as a sole carbon source (●: KO ΔldhA, ▲: KO ΔdhA ΔbudC, ■: KO ΔldhA Δdar. ◆:KO ΔldhA ΔbudC Δdar.)

As a result, strains (KO ΔldhA and KO ΔldhA ΔbudC) containing a dar gene encoding AR2 in the genome grew using 2,3-butanediol as a carbon source, and the concentration of the residual 2,3-butanediol was decreased in accordance with the growth. On the contrary, strains (KO ΔldhA Δdar and KO ΔldhA ΔbudC Δdar) with deleted dar gene did not grow over 200 hours' cultivation. The concentration of the residual 2,3-butanediol was maintained at initial cultivation concentration. Namely, it was confirmed that the recombinant strains can utilize or cannot utilize 2,3-butanediol as a carbon source depending on the presence of AR2 gene (dar) regardless of the presence of budC gene encoding AR1 (FIG. 6: Growth result. ■: KO ΔldhA, ▲: KO ΔldhA ΔbudC, ■: KO ΔldhA Δdar. ♦: KO ΔldhA ΔbudC Δdar. FIG. 7: Concentration of the residual 2,3-butanediol. ■: KO ΔldhA, ▲: KO ΔldhA ΔbudC, ■: KO ΔldhA Δdar. 4: KO ΔldhA ΔbudC Δdar.).

Accordingly, it was determined that AR2 played the key role in the two pathways of 2,3-butanediol consumption. Further, it was confirmed that AR2 functioned as a 2,3-butanediol dehydrogenase capable of converting 2,3-butanediol into acetoin in the cells.

To summarize the results of Experimental Examples 1 and 2, it was confirmed that AR2 has conversion activity between acetoin and 2,3-butanediol, and the activity for converting 2,3-butanediol into acetoin was higher than the activity for converting acetoin into 2,3-butanediol. On the other hand, it was also confirmed that AR1 has conversion activity between acetoin and 2,3-butanediol, and the activity for converting acetoin into 2,3-butanediol was higher than the activity for converting 2,3-butanediol into acetoin.

EXPERIMENTAL EXAMPLE 5

Production of 2,3-butanediol

The recombinant strains constructed in Experimental Example 3 were cultured, thereby producing 2,3-butanediol. As a control for comparison, *Klebsiella oxytoca* KCTC 12133BP ΔldhA (KO ΔldhA) was used.

Each recombinant strain was plated onto 250 ml of a composite medium containing 9 g/L glucose (50 mM, glucose), followed by culturing at 37° C. for 16 hours. 3 L of composite medium was inoculated with the resulting culture solution, and subjected to fermentation. The fermentation conditions were as follows: microaerobic conditions (aerobic speed of 1 vvm, stirring rate of 400 rpm), 90 g/L of initial glucose concentration, pH 6.8, a cultivation temperature of 37° C. While fermenting, 5N NaOH was used in order to adjust pH. Samples were taken while fermenting using the recombinant *Klebsiella*. The growth rate was determined by measuring OD600 (optical density) of the sampled specimens. The sampled specimens were subjected to centrifugation at 13,000 rpm for 10 minutes, followed by assaying the concentration of metabolites and 2,3-butanediol in the supernatant by high performance liquid chromatography (HPLC).

Figure 8:
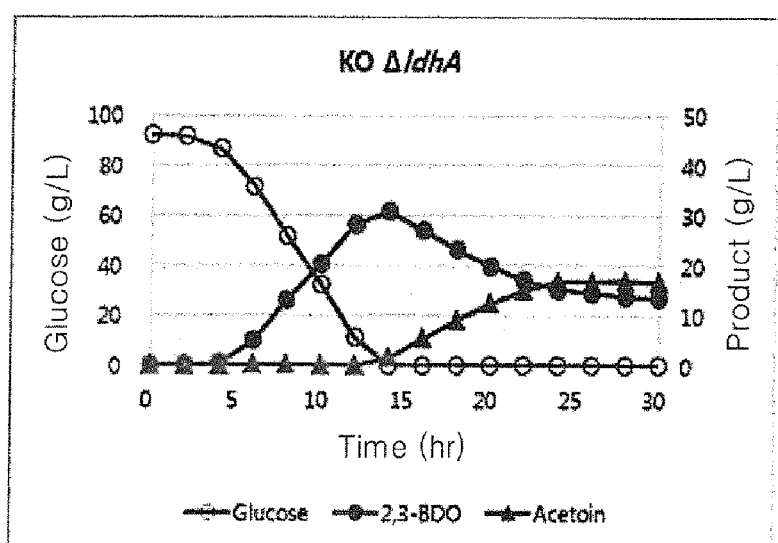
FIGS. 8 to 11 show the results of 2,3-butanediol production by batch fermentation of the recombinant strains of *Klebsiella* (FIG. 8: KO ΔldhA, FIG. 9: KO ΔldhA ΔbudC, FIG. 10: KO ΔldhA Δdar, FIG. 11: KO ΔldhA ΔbudC Δdar).
Figure 9:
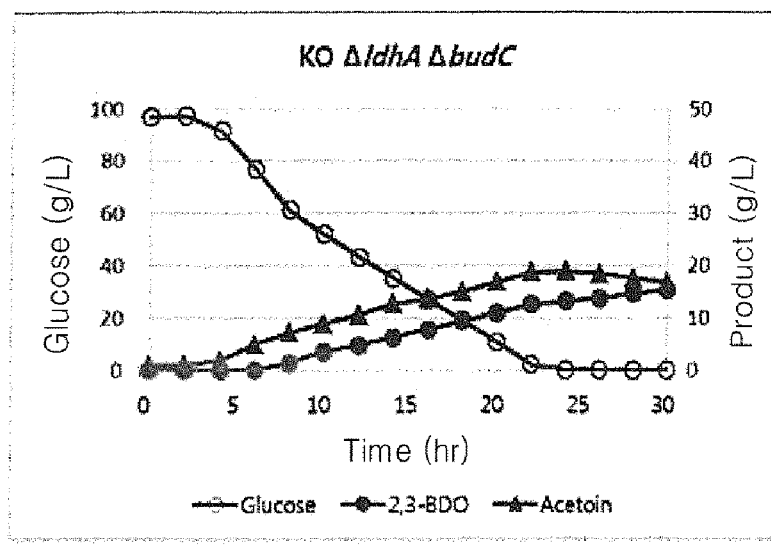
Figure 10:
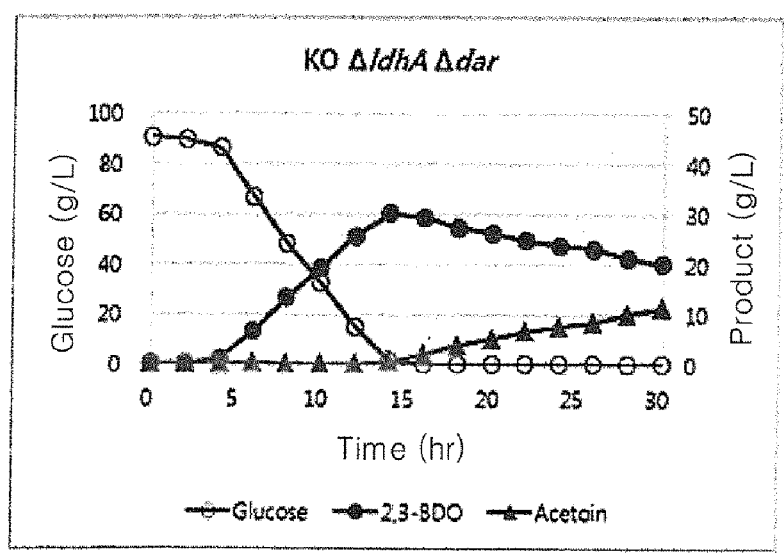
Figure 11:
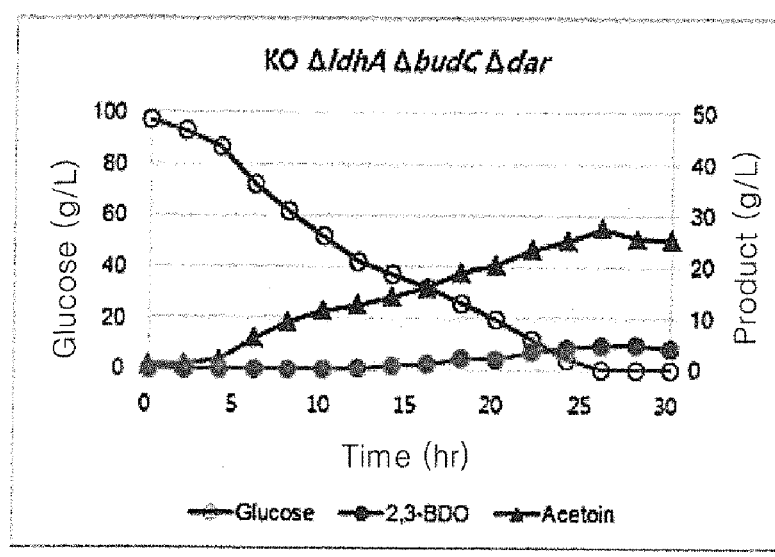

As a result, a recombinant strain (KO ΔldhA ΔbudC) with deleted AR1 gene exhibited lower 2,3-butanediol productivity than the strain KO ΔldhA (FIG. 8) as a comparative example, whereas the strain (KO ΔldhA ΔbudC) exhibited larger acetoin accumulation than the strain KO ΔldhA (FIG. 9). On the contrary, during consumption of sugar, a recombinant strain (KO ΔldhA Δdar) with deleted AR2 gene exhibited similar 2,3-butanediol productivity to the strain KO ΔldhA as a comparative example. After completion of sugar consumption, the consumption rate of 2,3-butanediol and the accumulation rate of acetoin were lower than those of comparative examples (FIG. 10). Strains with both AR1 and AR2 genes deleted showed almost no ability to produce 2,3-butanediol and high ability to produce acetoin (FIG. 11). Therefore, it was confirmed that strains with AR1 gene but AR2 gene deleted (KO ΔldhA Δdar) were highly advantageous in view of 2,3-butanediol production and storage after completion of fermentation (Table 5).

TABLE 5

| | Cultivation Time | | | |
| --- | --- | --- | --- | --- |
| | 14 hrs | | 30 hrs | |
| Strains | 2,3-butanediol (g/L) | Acetoin (g/L) | 2,3-butanediol (g/L) | Acetoin (g/L) |
| KO ΔldhA | 30.8 | 1.7 | 13.5 | 16.6 |
| KO ΔldhA ΔbudC | 6.2 | 12.7 | 15.4 | 16.7 |
| KO ΔldhA Δdar | 30.2 | 0.4 | 20.0 | 11.2 |
| KO ΔldhA ΔbudC Δdar | 0.6 | 14.1 | 4.0 | 25.3 |

INDUSTRIAL APPLICABILITY

The present invention relates to a recombinant microorganism having an enhanced ability to produce 2,3-butanediol and a method for producing 2,3-butanediol using the same.

Brief Description of the Sequences Provided in the Sequence

SEQ ID NO: 1 is a nucleotide sequence of ldhA gene, SEQ ID NO: 2 is a homologous region 1 of ldhA gene, SEQ ID NOs: 3 and 4 are primers for amplification of the homologous region 1 of ldhA gene. SEQ ID NO: 5 is a homologous region 2 of ldhA gene, SEQ ID NOs: 6 and 7 are primers for PCR amplification of the homologous region 2 of ldhA gene, SEQ ID NO: 8 is a DNA fragment in which the homologous regions 1 and 2 of ldhA gene are ligated.

SEQ ID NO: 9 is an amino acid sequence of AR1, SEQ ID NO: 10 is a nucleotide sequence of budC gene that encodes AR1.

SEQ ID NO: 11 is an amino acid sequence of AR2, SEQ ID NO: 12 is a nucleotide sequence of dar gene that encodes AR2.

SEQ ID NO: 13 is a homologous region 1 of the budC gene, SEQ ID NOs: 14 and 15 are primers for PCR amplification of the homologous region 1 of the budC gene. SEQ ID NO: 16 is a homologous region 2 of the budC gene, SEQ ID NOs: 17 and 18 are primers for PCR amplification of the homologous region 2 of the budC gene. SEQ ID NO: 19 is a DNA fragment in which the homologous regions 1 and 2 of the budC gene are ligated.

SEQ ID NO: 20 is a homologous region 1 of the dar gene, SEQ ID NOs: 21 and 22 are primers for PCR amplification of the homologous region 1 of the dar gene. SEQ ID NO: 23 is a homologous region 2 of the dar gene, SEQ ID NOs: 24 and 25 are primers for PCR amplification of the homologous region 2 of the dar gene. SEQ ID NO: 26 is a DNA fragment in which the homologous regions 1 and 2 of the dar gene are ligated.

The invention claimed is:

1. A recombinant microorganism having suppressed activity of the protein which has an amino acid sequence of SEQ ID NO: 11 in comparison to a wild type microorganism, wherein the microorganism is *Klebsiella*.

2. A recombinant microorganism having an enhanced ability to produce 2,3-butanediol, in comparison to a wild type microorganism, wherein activity of the protein which is encoded by the gene that has a nucleotide sequence of SEQ ID NO: 12 is suppressed in a microorganism having 2,3-butanediol and lactate biosynthetic pathways, wherein the microorganism is *Klebsiella*.

3. The recombinant microorganism according to claim 2, wherein a pathway of converting pyruvate into lactate is further suppressed.

4. The recombinant microorganism according to claim 2, wherein activity of lactate dehydrogenase is further suppressed.

5. The recombinant microorganism according to claim 2, wherein ldhA gene that encodes lactate dehydrogenase is deleted.

* * * * *

SEQUENCE LISTING

```
<160> NUMBER OF SEQ ID NOS: 29

<210> SEQ ID NO 1
<211> LENGTH: 990
<212> TYPE: DNA
<213> ORGANISM: Klebsiella oxytoca

<400> SEQUENCE: 1
atgaaaatcg ctgtgtatag tacaaaacag tacgacaaga agtatctgca gcatgttaat      60
gatgcatatg gctttgaact ggagttttt gacttcctgc taaccgaaaa aaccgccaaa     120
accgccaacg gctgtgaagc ggtgtgtatc ttcgtaaacg atgacggtag ccgcccggta     180
cttgaagaac tgaaagccca cggcgtgcag tacatcgcgc tgcgctgcgc ggggttcaac     240
aacgttgacc tcgatgccgc caaagagctg ggcctgcggg tggtgcgcgt cccggcctac     300
tcgccggaag cggtcgctga gcacgcgatc ggcatgatga tgtcgctgaa ccgccgcatt     360
caccgtgcct atcagcgcac ccgcgacgcg aacttctctc tggaagggct gaccggtttc     420
accatgcacg gtaaaaccgc cggcgttatt ggcaccggta aaatcggcgt cgccgcgctg     480
cgcattctta aaggcttcgg tatgcgtctg ctggcgtttg atccctaccc aagcgccgcc     540
gcgctggata tgggcgtgga gtatgtcgat cttgaaaccc tgtaccggga gtccgatgtt     600
atctcactgc actgcccact gaccgatgaa aactaccatt tgctgaacca tgccgcgttc     660
gatcgcatga aagacggggt gatgatcatc aacaccagcc gcggcgcgct catcgattcg     720
caggcagcga tcgacgccct gaagcatcag aaaattggcg cgctggggat ggacgtgtat     780
gagaacgaac gcgatctgtt ctttgaagat aagtctaatg acgtgattca ggatgatgtg     840
ttccgccgtc tctccgcctg ccataacgtc ctgtttaccg gtcaccaggc gtttctgacc     900
gcggaagcgt tgatcagcat ttcgcaaacc accctcgaca acctgcgtca agtggatgca     960
ggcgaaacct gtcctaacgc actggtctga                                     990

<210> SEQ ID NO 2
<211> LENGTH: 595
<212> TYPE: DNA
<213> ORGANISM: Artificial
<220> FEATURE:
<223> OTHER INFORMATION: a homologous region 1 of ldhA gene

<400> SEQUENCE: 2
atgacgttcg ctaaatcctg cgccgtcatc tcgctgctga tcccgggcac ctccgggcta      60
ctgctgttcg gcaccctggc atcggccagc ccgggacatt tcctgttaat gtggatgagc     120
```

```
gccagcctcg gcgctatcgg cggattctgg ctctcgtggc tgacgggcta ccgctaccgg      180
taccatctgc atcgtatccg ctggcttaat gccgaacgcc tcgctcgcgg ccagttgttc      240
ctgcgccgcc acggcgcgtg ggcagtcttt tttagccgct ttctctctcc gcttcgcgcc      300
accgtgccgc tggtaaccgg cgccagcggc acctctctct ggcagtttca gctcgccaac      360
gtcagctccg ggctgctctg ccgctgatcc tgctggcgc caggcgcgtt aagcctcagc       420
ttttgatgaa aggtattgtc ttttaaagag atttcttaac accgcgatat gctctagaat      480
tattactata acctgctgat taaactagtt tttaacattt gtaagattat tttaattatg      540
ctaccgtgac ggtattatca ctggagaaaa gtcttttttc cttgcccttt tgtgc          595
```

<210> SEQ ID NO 3
<211> LENGTH: 30
<212> TYPE: DNA
<213> ORGANISM: Artificial
<220> FEATURE:
<223> OTHER INFORMATION: a primer for amplification of a homologous
      region 1 of ldhA gene

<400> SEQUENCE: 3

```
cacggatcca tgacgttcgc taaatcctgc                                       30
```

<210> SEQ ID NO 4
<211> LENGTH: 40
<212> TYPE: DNA
<213> ORGANISM: Artificial
<220> FEATURE:
<223> OTHER INFORMATION: a primer for amplification of a homologous
      region 1 of ldhA gene

<400> SEQUENCE: 4

```
gcacaaaagg gcaaggaaaa aagactttc tccagtgata                             40
```

<210> SEQ ID NO 5
<211> LENGTH: 591
<212> TYPE: DNA
<213> ORGANISM: Artificial
<220> FEATURE:
<223> OTHER INFORMATION: a homologous region 2 of ldhA gene

<400> SEQUENCE: 5

```
tatcactgga gaaagtctt ttttccttgc ccttttgtgc tcccccttcg cggggggcac       60
attcagataa tccccacaga aattgcctgc gataaagtta caatcccttc atttattaat      120
acgataaata tttatggaga ttaaatgaac aagtatgctg cgctgctggc ggtgggaatg      180
ttgctatcgg gctgcgttta taacagcaag gtgtcgacca gagcggaaca gcttcagcac      240
caccgttttg tgctgaccag cgttaacggg cagccgctga atgccgcgga taagccgcag      300
gagctgagct tcggcgaaaa gatgcccatt acgggcaaga tgtctgtttc aggtaatatg      360
tgcaaccgct tcagcggcac gggcaaagtc tctgacggcg agctgaaggt tgaagagctg      420
gcaatgaccc gcatgctctg cacggactcg cagcttaacg ccctggacgc cacgctgagc      480
aaaatgctgc gcgaaggcgc gcaggtcgac ctgacgaaaa cgcagctaac gctggcgacc      540
gccgaccaga cgctggtgta aagctcgcc gacctgatga attaataatt a                591
```

<210> SEQ ID NO 6
<211> LENGTH: 40
<212> TYPE: DNA
<213> ORGANISM: Artificial

<220> FEATURE:
<223> OTHER INFORMATION: a primer for amplification of a homologous
      region 2 of ldhA gene

<400> SEQUENCE: 6
tatcactgga gaaaagtctt ttttccttgc ccttttgtgc                          40

<210> SEQ ID NO 7
<211> LENGTH: 32
<212> TYPE: DNA
<213> ORGANISM: Artificial
<220> FEATURE:
<223> OTHER INFORMATION: a primer for amplification of a homologous
      region 2 of ldhA gene

<400> SEQUENCE: 7
cctgcggccg ctaattatta attcatcagg tc                                  32

<210> SEQ ID NO 8
<211> LENGTH: 1146
<212> TYPE: DNA
<213> ORGANISM: Artificial
<220> FEATURE:
<223> OTHER INFORMATION: a DNA fragment in which the homologous regions
      1 and 2 of ldhA gene are ligated

<400> SEQUENCE: 8
atgacgttcg ctaaatcctg cgccgtcatc tcgctgctga tcccgggcac ctccgggcta    60
ctgctgttcg gcaccctggc atcggccagc ccgggacatt tcctgttaat gtggatgagc   120
gccagcctcg cgctatcgg cggattctgg ctctcgtggc tgacgggcta ccgctaccgg    180
taccatctgc atcgtatccg ctggcttaat gccgaacgcc tcgctcgcgg ccagttgttc   240
ctgcgccgcc acggcgcgtg gcagtctttt ttagccgct ttctctctcc gcttcgcgcc    300
accgtgccgc tggtaaccgg cgccagcggc acctctctct ggcagtttca gctcgccaac   360
gtcagctccg gctgctctg ccgctgatc ctgctggcgc caggcgcgtt aagcctcagc     420
ttttgatgaa aggtattgtc ttttaaagag atttcttaac accgcgatat gctctagaat   480
tattactata acctgctgat taaactagtt tttaacattt gtaagattat tttaattatg   540
ctaccgtgac ggtattatca ctggagaaaa gtcttttttc cttgcccttt tgtgctcccc   600
cttcgcgggg ggcacattca gataatcccc acagaaattg cctgcgataa agttacaatc   660
ccttcattta ttaatacgat aaatatttat ggagattaaa tgaacaagta tgctgcgctg   720
ctggcggtgg aatgttgct atcgggctgc gtttataaca gcaaggtgtc gaccagagcg    780
gaacagcttc agcaccaccg ttttgtgctg accagcgtta acgggcagcc gctgaatgcc   840
gcggataagc gcaggagct gagcttcggc gaaaagatgc ccattacggg caagatgtct   900
gtttcaggta atatgtgcaa ccgcttcagc ggcacgggca agtctctga cggcgagctg    960 aaggttgaag agctggcaat gacccgcatg ctctgcacgg actcgcagct taacgccctg   1020
gacgccacgc tgagcaaaat gctgcgcgaa ggcgcgcagg tcgacctgac ggaaacgcag   1080
ctaacgctgg cgaccgccga ccagacgctg gtgtataagc tcgccgacct gatgaattaa   1140
taatta                                                              1146

<210> SEQ ID NO 9
<211> LENGTH: 256
<212> TYPE: PRT
<213> ORGANISM: Klebsiella oxytoca

<400> SEQUENCE: 9

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Gln Ala Val Ala Asp Glu Ile Asn Arg
        35                  40                  45

Ser Gly Gly Arg Ala Leu Ala Val Lys Val Asp Val Ser Gln Arg Asp
    50                  55                  60

Gln Val Phe Ala Ala Val Glu Gln Ala Arg Lys Gly Leu Gly Gly Phe
65                  70                  75                  80

Asp Val Ile Val Asn Asn Ala Gly Val Ala Pro Ser Thr Pro Ile Glu
                85                  90                  95

Glu Ile Arg Glu Glu Val Ile Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala His Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Gln Glu Phe Ala Lys Arg Ile Thr Leu Gly Arg Leu Ser Glu Pro
    210                 215                 220

Glu Asp Val Ala Ala Cys Val Ser Tyr Leu Ala Gly Pro Asp Ser Asn
225                 230                 235                 240

Tyr Met Thr Gly Gln Ser Leu Leu Ile Asp Gly Gly Met Val Phe Asn
                245                 250                 255
```

<210> SEQ ID NO 10
<211> LENGTH: 768
<212> TYPE: DNA
<213> ORGANISM: Klebsiella oxytoca

<400> SEQUENCE: 10

```
atgaaaaaag tcgcactcgt caccggcgcg ggccagggta tcggtaaagc tatcgccctt    60
cgtctggtga agatggtttt tgccgtggct atcgccgatt ataacgacgc caccgcgcag   120
gcggtcgctg atgaaattaa ccgcagcggc ggccgggcgc tagcggtgaa ggtggatgtg   180
tctcaacgcg atcaggtttt tgccgccgtc gaacaggcgc gcaagggtct cggcggtttt   240
gacgtgatcg tcaacaacgc cggggttgcg ccctccacac caatcgaaga gattcgcgag   300
gaggtgatcg ataaagtcta caatatcaac gttaaaggcg ttatctgggg catccaggcc   360
gcggtagagg cgtttaaaaa agagggccac ggcggcaaaa ttatcaacgc ctgctcccag   420
gcgggccatg taggtaaccc ggagctggcg gtctatagct ccagtaaatt tgccgtgcgc   480
ggcctgacgc aaaccgccgc ccgcgatctg gcgcatctgg ggattaccgt aaacggctac   540
tgccccggga tcgtcaaaac cccaatgtgg gcggaaattg accgccaggt ttccgaagcg   600
gcgggtaaac cgctgggcta cggaacccag gagttcgcca aacgcattac ccttgggcgg   660
```

```
ctatccgagc cggaagacgt cgcagcctgc gtctcttatc tcgccggtcc ggactccaat      720
tatatgaccg ccaatcgct gctgatcgat ggcggcatgg tatttaac                    768
```

<210> SEQ ID NO 11
<211> LENGTH: 259
<212> TYPE: PRT
<213> ORGANISM: Klebsiella oxytoca

<400> SEQUENCE: 11

```
Met Ala Ile Glu Asn Lys Val Ala Leu Val Thr Gly Ala Gly Gln Gly
1               5                   10                  15
Ile Gly Arg Gly Ile Ala Leu Arg Leu Ala Lys Asp Gly Ala Ser Val
                20                  25                  30
Met Leu Val Asp Val Asn Pro Glu Gly Ile Ala Ala Val Ala Ala Glu
            35                  40                  45
Val Glu Ala Leu Gly Arg Lys Ala Ala Thr Phe Val Ala Asn Ile Ala
        50                  55                  60
Asp Arg Ala Gln Val Tyr Ala Ala Ile Asp Glu Ala Glu Lys Gln Leu
65                  70                  75                  80
Gly Gly Phe Asp Ile Ile Val Asn Asn Ala Gly Ile Ala Gln Val Gln
                85                  90                  95
Ala Leu Ala Asp Val Thr Pro Glu Glu Val Asp Arg Ile Met Arg Ile
            100                 105                 110
Asn Val Gln Gly Thr Leu Trp Gly Ile Gln Ala Ala Lys Lys Phe
        115                 120                 125
Ile Asp Arg Gln Gln Lys Gly Lys Ile Ile Asn Ala Cys Ser Ile Ala
130                 135                 140
Gly His Asp Gly Phe Ala Leu Leu Gly Val Tyr Ser Ala Thr Lys Phe
145                 150                 155                 160
Ala Val Arg Ala Leu Thr Gln Ala Ala Ala Lys Glu Tyr Ala Ser Arg
                165                 170                 175
Gly Ile Thr Val Asn Ala Tyr Cys Pro Gly Ile Val Gly Thr Gly Met
            180                 185                 190
Trp Thr Glu Ile Asp Lys Arg Phe Ala Glu Ile Thr Gly Ala Pro Val
        195                 200                 205
Gly Glu Thr Tyr Lys Lys Tyr Val Glu Gly Ile Ala Leu Gly Arg Ala
    210                 215                 220
Glu Thr Pro Asp Asp Val Ala Ser Leu Val Ser Tyr Leu Ala Gly Pro
225                 230                 235                 240
Asp Ser Asp Tyr Val Thr Gly Gln Ser Ile Leu Ile Asp Gly Gly Ile
                245                 250                 255
Val Tyr Arg
```

<210> SEQ ID NO 12
<211> LENGTH: 777
<212> TYPE: DNA
<213> ORGANISM: Klebsiella oxytoca

<400> SEQUENCE: 12

```
atggctatcg aaaataaagt tgcgctggta accggcgccg gtcagggcat tggccgcggt      60
attgcgttgc gtctggccaa agacggcgcg tcggtgatgc tggtcgacgt gaaccctgaa     120
gggattgccg ccgtcgccgc cgaagtggaa gcgctgggac gcaaagcagc caccttcgtc     180
gctaacatcg ccgatcgcgc gcaggtgtac gccgccattg atgaagcgga aaaacagctg     240
ggcggctttg atattatcgt gaacaacgcc gggatcgccc aggttcaggc gctggccgat     300
```

```
gtgacgcctg aagaagtgga ccgcatcatg cgcatcaacg ttcagggtac cctgtggggt    360
attcaggcgg cggcgaaaaa attcatcgat cgtcagcaga aagggaaaat catcaacgcc    420
tgctctatcg ccggtcatga tggtttcgcg ctgctgggcg tttattccgc caccaaattt    480
gccgtacgcg ccctgacgca ggcggcggcg aaggagtatg ccagccgcgg cattacggtt    540
aatgcctact gtccggggat tgtgggaacc gggatgtgga ccgaaatcga taagcgcttt    600
gcggaaatta ccggtgcgcc ggtgggcgaa acttataaaa aatacgttga aggcatcgcc    660
cttggccgcg ccgaaacgcc ggacgatgtg gcaagcctgg tctcttatct ggcaggcccg    720
gattccgatt atgttaccgg tcagtcgatt ctgatcgatg cggtattgt ttaccgt        777
```

<210> SEQ ID NO 13
<211> LENGTH: 640
<212> TYPE: DNA
<213> ORGANISM: Artificial
<220> FEATURE:
<223> OTHER INFORMATION: a homologous region 1 of the budC gene

<400> SEQUENCE: 13

```
gctgcgcatc gttcgcgcca tgcaggacat cgtcaatagc gatgtcaccc tgaccgtcga    60
tatggggagc tttcatatct ggatcgcccg ctatctctac agctttcgcg cccgtcaggt    120
catgatttcc aacggtcaac agaccatggg cgtggcgctg ccgtgggcga ttggcgcctg    180
gctggtcaat ccgcagcgca aagtggtttc cgtttccggc gacggcggtt tcctgcagtc    240
cagcatggag ctggagaccg ctgtacggct gaaagcgaac gtcctgcata tcatctgggt    300
cgataacggc tacaacatgg tggcgattca ggaggagaaa aaataccagc ggctctccgg    360
cgttgagttc ggcccggtgg atttttaaagt ctacgccgaa gccttcggcg ccaaagggtt    420
tgcggtagag agcgccgaag cccttgagcc gacgctgcgg gcggcgatgg acgtcgacgg    480
ccccgccgtc gtagccatcc ccgtggatta ccgcgataac ccgctgctga tgggccagct    540
ccatctcagt caactacttt gagtcactac agaaggaatc tatcaatgaa aaaagtcgca    600
ctcgtgaccg gcgcgatgac cggccaatcg ctgctgatcg                         640
```

<210> SEQ ID NO 14
<211> LENGTH: 29
<212> TYPE: DNA
<213> ORGANISM: Artificial
<220> FEATURE:
<223> OTHER INFORMATION: a primer for amplification of a homologous
      region 1 of the budC gene

<400> SEQUENCE: 14

```
ggatccgctg cgcatcgttc gcgccatgc                                      29
```

<210> SEQ ID NO 15
<211> LENGTH: 48
<212> TYPE: DNA
<213> ORGANISM: Artificial
<220> FEATURE:
<223> OTHER INFORMATION: a primer for amplification of a homologous
      region 1 of the budC gene

<400> SEQUENCE: 15

```
cgatcagcag cgattggccg gtcatcgcgc cggtcacgag tgcgactt                 48
```

<210> SEQ ID NO 16
<211> LENGTH: 606
<212> TYPE: DNA
<213> ORGANISM: Artificial

```
<220> FEATURE:
<223> OTHER INFORMATION: a homologous region 2 of the budC gene

<400> SEQUENCE: 16
aagtcgcact cgtgaccggc gcgatgaccg gccaatcgct gctgatcgat ggcggcatgg      60
tatttaacta ataataaata agctctgaca tggtttgccc cggcgtcacc gccgggcttt     120
ttttatttca acctttaggg aagatccaca ggtcgctgac gggcaatgtc agatggcaac    180
gctcggcatc gcgcagcgcg ctgccgtagg cgcgtatggc gaaatcatcg ccttcagtgc    240
gaaacagata ctcccagcgg tcgccgaggt acatgctggt caacagcggc agcgccagca    300
tgttctcttc aggcgcggaa gcgatgcgca aacgctcaac gcggatcacc gccgtcgcct    360
cttcccccac gctaacccct tccccgcca ttccccatag cgcccagctg gccccctcaa     420
tgcgcgcccg accgttctcc agcgcgctaa cggtgccatg caggcgatta ttactgccca    480
taaactcggc ggcaaacagc gttttcgggc tgccgtacat ctcctgcggg gttccctgct    540
gctcgatcac gccgttgtta agcagcagaa tgcgatcgga aatcgccatc gcctcgttct    600
gatcgt                                                                606

<210> SEQ ID NO 17
<211> LENGTH: 48
<212> TYPE: DNA
<213> ORGANISM: Artificial
<220> FEATURE:
<223> OTHER INFORMATION: a primer for PCR amplification of the
      homologous region 2 of the budC gene

<400> SEQUENCE: 17
aagtcgcact cgtgaccggc gcgatgaccg gccaatcgct gctgatcg                   48

<210> SEQ ID NO 18
<211> LENGTH: 33
<212> TYPE: DNA
<213> ORGANISM: Artificial
<220> FEATURE:
<223> OTHER INFORMATION: a primer for PCR amplification of the
      homologous region 2 of the budC gene

<400> SEQUENCE: 18
gcggccgcac gatcagaacg aggcgatggc gat                                   33

<210> SEQ ID NO 19
<211> LENGTH: 1198
<212> TYPE: DNA
<213> ORGANISM: Artificial
<220> FEATURE:
<223> OTHER INFORMATION: a DNA fragment in which the homologous regions
      1 and 2 of the budC gene are ligated

<400> SEQUENCE: 19
gctgcgcatc gttcgcgcca tgcaggacat cgtcaatagc gatgtcaccc tgaccgtcga      60 tatgggagc tttcatatct ggatcgcccg ctatctctac agctttcgcg cccgtcaggt    120
catgatttcc aacggtcaac agaccatggg cgtggcgctg ccgtgggcga ttggcgcctg    180
gctggtcaat ccgcagcgca aagtggtttc cgtttccggc gacggcggtt tcctgcagtc    240
cagcatggag ctggagaccg ctgtacggct gaaagcgaac gtcctgcata tcatctgggt    300
cgataacggc tacaacatgg tggcgattca ggaggagaaa aaataccagc ggctctccgg    360
cgttgagttc ggcccggtgg atttaaagt ctacgccgaa gccttcggcg ccaaagggtt     420
tgcggtagag agcgccgaag cccttgagcc gacgctgcgg gcggcgatgg acgtcgacgg    480
```

| | |
|---|---|
| cccccgccgtc gtagccatcc ccgtggatta ccgcgataac ccgctgctga tgggccagct | 540 |
| ccatctcagt caactacttt gagtcactac agaaggaatc tatcaatgaa aaaagtcgca | 600 |
| ctcgtgaccg gcgcgatgac cggccaatcg ctgctgatcg atggcggcat ggtatttaac | 660 |
| taataataaa taagctctga catgctttgc cccggcgtca ccgccggggc ttttttattt | 720 |
| caacctttag ggaagatcca caggtcgctg acgggcaatg tcagatggca acgctcggca | 780 |
| tcgcgcagcg cgctgccgta ggcgcgtatg gcgaaatcat cgccttcagt gcgaaacaga | 840 |
| tactcccagc ggtcgccgag gtacatgctg gtcaacagcg gcagcgccag catgttctct | 900 |
| tcaggcgcgg aagcgatgcg caaacgctca acgcggatca ccgccgtcgc ctcttccccc | 960 |
| acgctaaccc cttccccgc cattccccat agcgcccagc tggccccctc aatgcgcgcc | 1020 |
| cgaccgttct ccagcgcgct aacggtgcca tgcaggcgat tattactgcc cataaactcg | 1080 |
| gcggcaaaca gcgttttcgg gctgccgtac atctcctgcg gggttccctg ctgctcgatc | 1140 |
| acgccgttgt taagcagcag aatgcgatcg gaaatcgcca tcgcctcgtt ctgatcgt | 1198 |

<210> SEQ ID NO 20
<211> LENGTH: 621
<212> TYPE: DNA
<213> ORGANISM: Artificial
<220> FEATURE:
<223> OTHER INFORMATION: a homologous region 1 of the dar gene

<400> SEQUENCE: 20

| | |
|---|---|
| ggaggtcggc cggaagctcg ccttgcagca gctgcagaaa cgacgggctc caccccctgcc | 60 |
| acaagggccg cagcgcctcc tgcagatagc gtataaacag tagcggcgcg ttgtcatcct | 120 |
| cttcaaggct cagccaggcc agcgcatccc cttgtcgaag gcggtgtcga taccactgcg | 180 |
| ccagcagggt ggttttgcca atccggcgg gcgcgcgcac cagggttaaa cggcgggaga | 240 |
| cggcggcgtc gaggcgctgt agcaggcgct cccgcgatag cagactttcc ggcgtacggg | 300 |
| gcggcgtaaa gcgcgtggag ataagcggca gcgtccccgt gaagcgtaaa ggttcctgat | 360 |
| gaacaagcgc tgccagcgca tcatccgccg aggataaaaa ggccatacca cgattactcc | 420 |
| ttaatccagt ccgtacgctc attatccccc ccatcagggg ggtaggccac gcttatcgcg | 480 |
| cccgatagag tagtgccatt cgccgcagcg gctacgacga catcggccgc gggcctccct | 540 |
| agttttattaa tcagtacaag gtgagtacag acatggctat cgaaaataaa gttgcgaccg | 600 |
| gtcagtcgat tctgatcgat g | 621 |

<210> SEQ ID NO 21
<211> LENGTH: 34
<212> TYPE: DNA
<213> ORGANISM: Artificial
<220> FEATURE:
<223> OTHER INFORMATION: a primer for PCR amplification of the
    homologous region 1 of the dar gene

<400> SEQUENCE: 21

| | |
|---|---|
| tctagaggat ccggaggtcg gccggaagct cgcc | 34 |

<210> SEQ ID NO 22
<211> LENGTH: 52
<212> TYPE: DNA
<213> ORGANISM: Artificial
<220> FEATURE:
<223> OTHER INFORMATION: a primer for PCR amplification of the
    homologous region 1 of the dar gene

<400> SEQUENCE: 22
catcgatcag aatcgactga ccggtcgcaa ctttattttc gatagccatg tc        52

<210> SEQ ID NO 23
<211> LENGTH: 608
<212> TYPE: DNA
<213> ORGANISM: Artificial
<220> FEATURE:
<223> OTHER INFORMATION: a homologous region 2 of the dar gene

<400> SEQUENCE: 23
gacatggcta tcgaaaataa agttgcgacc ggtcagtcga ttctgatcga tggcggtatt    60
gtttaccgtt aagggataaa cccggcgcag aacgcgccgg ttttttgcgg ggttacgcgt   120
tagccgcggg ctcctgcggc ttgtcgctac gggtgttttc cagcatccgg cgaaccggaa   180
caatcagcag gcacagcacc gcggcgcaga tcagcagcgc aatagagcag cgtgcgaaca   240
ggtcgggcag catatccagc tgatcggcct tcacgtgacc gccaatcaga cccgccgcca   300
ggttccccag ggcgctggcg cagaaccaca gccccatcat ctggccgcgc attctttccg   360
gcgccagcag cgtcatggtc gcgaggccaa tcgggctgag gcacagctcg cccagcgtca   420
gcatcagaat actgcccacc agccacatcg gcgagacgcc cgcgccgttg ttgctcagga   480
cgttttgcgc cgccagcatc atcaggccaa agcccgccgc cgcgcataaa ataccgataa   540
caaacttggt gatgctgctc ggacgcacgt ttttacgcgc cagcgcaggc cacgcccagc   600
taaatacc                                                         608

<210> SEQ ID NO 24
<211> LENGTH: 52
<212> TYPE: DNA
<213> ORGANISM: Artificial
<220> FEATURE:
<223> OTHER INFORMATION: a primer for PCR amplification of the
      homologous region 2 of the dar gene

<400> SEQUENCE: 24
gacatggcta tcgaaaataa agttgcgacc ggtcagtcga ttctgatcga tg        52

<210> SEQ ID NO 25
<211> LENGTH: 35
<212> TYPE: DNA
<213> ORGANISM: Artificial
<220> FEATURE:
<223> OTHER INFORMATION: a primer for PCR amplification of the
      homologous region 2 of the  dar gene

<400> SEQUENCE: 25
atcgcggccg cggtatttag ctgggcgtgg cctgc                              35

<210> SEQ ID NO 26
<211> LENGTH: 1177
<212> TYPE: DNA
<213> ORGANISM: Artificial
<220> FEATURE:
<223> OTHER INFORMATION: a DNA fragment in which the homologous regions
      1 and 2 of the dar gene are ligated

<400> SEQUENCE: 26
ggaggtcggc cggaagctcg ccttgcagca gctgcagaaa cgacgggctc caccctgcc    60 acaagggccg cagcgcctcc tgcagatagc gtataaacag tagcggcgcg ttgtcatcct   120
cttcaaggct cagccaggcc agcgcatccc cttgtcgaag gcggtgtcga taccactgcg   180

-continued

```
ccagcagggt ggttttgcca atccggcgg gcgcgcgcac cagggttaaa cggcgggaga         240
cggcggcgtc gaggcgctgt agcaggcgct cccgcgatag cagactttcc ggcgtacggg         300
gcggcgtaaa gcgcgtggag ataagcggca gcgtccccgt gaagcgtaaa ggttcctgat         360
gaacaagcgc tgccagcgca tcatccgccg aggataaaaa ggccatacca cgattactcc         420
ttaatccagt ccgtacgctc attatccccc ccatcagggg ggtaggccac gcttatcgcg         480
cccgatagag tagtgccatt cgccgcagcg gctacgacga catcggccgc gggcctccct         540
agtttattaa tcagtacaag gtgagtacag acatggctat cgaaaataaa gttgcgaccg         600
gtcagtcgat tctgatcgat ggcggtattg tttaccgtta agggataaac ccggcgcaga         660
acgcgccggg tttttgcggg gttacgcgtt agccgcgggc tcctgcggct tgtcgctacg         720
ggtgttttcc agcatccggc gaaccggaac aatcagcagg cacagcaccg cggcgcagat         780
cagcagcgca atagagcagc gtgcgaacag gtcgggcagc atatccagct gatcggcctt         840
cacgtgaccg ccaatcagac ccgccgccag gttccccagg gcgctggcgc agaaccacag         900
ccccatcatc tggccgcgca ttctttccgg cgccagcagc gtcatggtcg cgaggccaat         960
cgggctgagg cacagctcgc ccagcgtcag catcagaata ctgcccacca gccacatcgg        1020
cgagacgccc gcgccgttgt tgctcaggac gttttgcgcc gccagcatca tcaggccaaa        1080
gcccgccgcc gcgcataaaa taccgataac aaacttggtg atgctgctcg gacgcacgtt        1140
tttacgcgcc agcgcaggcc acgcccagct aaatacc                                 1177
```

<210> SEQ ID NO 27
<211> LENGTH: 8
<212> TYPE: PRT
<213> ORGANISM: Artificial
<220> FEATURE:
<223> OTHER INFORMATION: a binding site for NADH of N-terminal of
      2,3-butanediol conversion enzyme
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 27

Thr Gly Xaa Xaa Xaa Gly Xaa Gly
1               5

<210> SEQ ID NO 28
<211> LENGTH: 4
<212> TYPE: PRT
<213> ORGANISM: Artificial
<220> FEATURE:
<223> OTHER INFORMATION: a catalytic tetrad of 2,3-butanediol conversion
      enzyme

<400> SEQUENCE: 28

Asn Ser Tyr Lys
1

<210> SEQ ID NO 29
<211> LENGTH: 5
<212> TYPE: PRT
<213> ORGANISM: Artificial
<220> FEATURE:
<223> OTHER INFORMATION: an active site of 2,3-butanediol conversion
      enzyme

```
<220> FEATURE:
<221> NAME/KEY: misc_feature
<222> LOCATION: (2)..(4)
<223> OTHER INFORMATION: Xaa can be any naturally occurring amino acid

<400> SEQUENCE: 29

Tyr Xaa Xaa Xaa Lys
1               5
```